United States Patent
Jubran et al.

(10) Patent No.: US 7,326,506 B2
(45) Date of Patent: Feb. 5, 2008

(54) BRIDGED CHARGE TRANSPORT MATERIALS HAVING A CENTRAL SULFUR ATOM LINKAGE

(75) Inventors: Nusrallah Jubran, St. Paul, MN (US); Zbigniew Tokarski, Woodbury, MN (US); Vytautas Getautis, Kaunas (LT); Juozas V. Grazulevicius, Kaunas (LT); Vygintas Jankauskas, Vilnius (LT); Ingrida Paulauskaite, Kaunas (LT); Jurate Simokaitiene, Kaunas (LT); Albina Stanisauskaite, Kaunas (LT); Valentas Gaidelis, Vilnius (LT)

(73) Assignee: Samsung Electronics Co., Ltd., Suwon, Kyungki-Do (KR)

( * ) Notice: Subject to any disclaimer, the term of this patent is extended or adjusted under 35 U.S.C. 154(b) by 403 days.

(21) Appl. No.: 10/857,267

(22) Filed: May 28, 2004

(65) Prior Publication Data

US 2005/0266329 A1    Dec. 1, 2005

(51) Int. Cl.
G03G 15/02 (2006.01)
G03G 15/00 (2006.01)
C07C 251/00 (2006.01)
C07C 259/00 (2006.01)

(52) U.S. Cl. .................. 430/58.4; 430/58.75; 399/159; 564/251; 564/305

(58) Field of Classification Search .............. 430/58.4, 430/58.7, 58.75, 79, 77, 73, 58.5; 399/159; 564/251, 305
See application file for complete search history.

(56) References Cited

U.S. PATENT DOCUMENTS

| | | | |
|---|---|---|---|
| 4,297,426 A | 10/1981 | Sakai et al. | |
| 4,786,571 A | 11/1988 | Ueda | |
| 5,942,615 A | 8/1999 | Kobayashi et al. | |
| 6,066,426 A | 5/2000 | Mott et al. | |
| 6,083,651 A | 7/2000 | Kobayashi et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,670,085 B2 | 12/2003 | Jubran et al. | |
| 6,689,523 B2 | 2/2004 | Law et al. | |
| 6,696,209 B2 | 2/2004 | Law et al. | |
| 6,749,978 B2 | 6/2004 | Jubran et al. | |
| 6,768,010 B1 | 7/2004 | Tokarski et al. | |
| 6,887,634 B2 * | 5/2005 | Jubran et al. | 430/58.6 |
| 7,112,391 B2 * | 9/2006 | Jubran et al. | 430/58.6 |
| 7,115,347 B2 * | 10/2006 | Tokarski et al. | 430/58.65 |
| 7,118,839 B2 * | 10/2006 | Law et al. | 430/58.15 |
| 2003/0113643 A1 * | 6/2003 | Law et al. | 430/58.15 |
| 2003/0129513 A1 * | 7/2003 | Jubran et al. | 430/73 |
| 2003/0232261 A1 | 12/2003 | Tokarski et al. | |
| 2004/0013959 A1 * | 1/2004 | Bender et al. | 430/56 |
| 2004/0241563 A1 * | 12/2004 | Danilevicius et al. | 430/76 |
| 2005/0147906 A1 * | 7/2005 | Jubran et al. | 430/79 |

FOREIGN PATENT DOCUMENTS

| | | |
|---|---|---|
| EP | 0694 532 | 1/1996 |
| JP | 09-302029 | 5/1996 |
| JP | 2001-166519 | 6/2001 |
| SU | 332113 | 12/1972 |
| SU | 386934 | 10/1973 |

OTHER PUBLICATIONS

Brittain et al., 1993, Tetrahedran Letters, vol. 34 No. 21, p. 3363.*
Korean Intellectual Property Office Notice to Submit Response, Examined by Hyunjin Jeong and Jeongsuk Jang, Mar. 2, 2006.*
Brittain et al., "Triphenylsilanethiol: A Solid $H_2S$ Equivalent in the Ring Opening of Epoxides", Tetrahedron Letters, 34(21):3363-3366 (XP-002345071).

* cited by examiner

Primary Examiner—Mark F. Huff
Assistant Examiner—Peter Vajda
(74) Attorney, Agent, or Firm—Peterson, Thuente, Skaar & Christensen, P.A.

(57) ABSTRACT

Improved organophotoreceptor comprises an electrically conductive substrate and a photoconductive element on the electrically conductive substrate, the photoconductive element comprising:

(a) a charge transport material having the formula

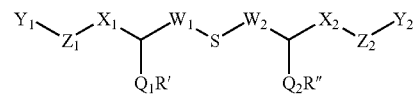

where $Z_1$ and $Z_2$ comprise, each independently, a bond, a vinyl group, a —$CR_1$=N—$NR_2$— group, or a —$CR_3$=N—N=$CR_4$— group;

$Y_1$ and $Y_2$ comprise, each independently, an aromatic group;

$X_1$ and $X_2$ are, each independently, a linking group;

$W_1$ and $W_2$ are, each independently, a —$(CH_2)_n$— group or a —$(CH_2)_{n-1}$—C(=O)— group, where n is an integer between 1 and 10, inclusive;

$Q_1$ and $Q_2$ are, each independently, O, S, or NR; and $R_1$, $R_2$, $R_3$, $R_4$, R, R', and R" comprise, each independently, H, an alkyl group, an alkenyl group, an alkynyl group, an acyl group, a heterocyclic group, or an aromatic group; and (b) a charge generating compound.

Corresponding electrophotographic apparatuses and imaging methods are described.

30 Claims, No Drawings

BRIDGED CHARGE TRANSPORT MATERIALS HAVING A CENTRAL SULFUR ATOM LINKAGE

FIELD OF THE INVENTION

This invention relates to organophotoreceptors suitable for use in electrophotography and, more specifically, to organophotoreceptors including a bridged charge transport material having two aromatic groups bonded together through linking groups and a central sulfur atom linkage.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising:

(a) a charge transport material having the formula:

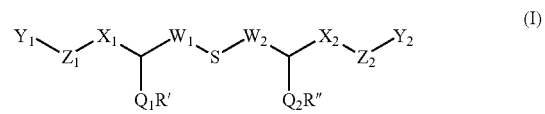

where $Z_1$ and $Z_2$ comprise, each independently, a bond, a vinyl group, a —$CR_1$=N—$NR_2$— group, or a —$CR_3$=N—N=$CR_4$— group where $R_1$, $R_2$, $R_3$, and $R_4$ comprise, each independently, H, an alkyl group, an alkenyl group, an alkynyl group, an acyl group, an aromatic group, or a heterocyclic group;

$Y_1$ and $Y_2$ comprise, each independently, an aromatic group;

$X_1$ and $X_2$ are, each independently, a linking group, such as a —$(CH_2)_m$— group, where m is an integer between 1 and 10, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkylsulfanyl group, an alkenyl group, an alkynyl group, an acyl group, a heterocyclic group, an aromatic group, or a part of a ring group, such as cycloalkyl groups, heterocyclic groups, or a benzo group;

$W_1$ and $W_2$ are, each independently, a —$(CH_2)_n$— group or a —$(CH_2)_n$— —C(=O)— group, where n is an integer between 1 and 10, inclusive;

$Q_1$ and $Q_2$ are, each independently, O, S, or NR; and

R, R', and R" are, each independently, H, an alkyl group, an alkenyl group, an alkynyl group, an acyl group, a heterocyclic group, or an aromatic group; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, a second charge transport material, and a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser, such as a liquid toner dispenser. The method of electrophotographic imaging with photoreceptors containing the above noted charge transport materials is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having Formula (I) above.

In a fifth aspect, the invention features a method of preparing a bridged charge transport material by reacting a bridging compound selected from the group consisting of sodium sulfide and thioacetamide with at least a compound having a reactive ring group comprising the following formula:

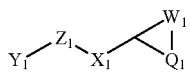

where $Z_1$ comprises a bond, a vinyl group, a —$CR_1$=N— $NR_2$— group, or a —$CR_3$=N—N=$CR_4$— group where $R_1$, $R_2$, $R_3$, and $R_4$ comprise, each independently, H, an alkyl group, an alkenyl group, an alkynyl group, an acyl group, an aromatic group, or a heterocyclic group;

$Y_1$ comprises an aromatic group;

$X_1$ is a linking group;

$W_1$ is a —$(CH_2)_n$— group or a —$(CH_2)_{n-1}$—C(=O)— group, where n is an integer between 1 and 10, inclusive; and $Q_1$ is O, S, or NR where R is H, an alkyl group, an alkenyl group, an alkynyl group, an acyl group, a heterocyclic group, or an aromatic group.

The invention provides suitable charge transport materials for organophotoreceptors featuring a combination of good mechanical and electrostatic properties. These photoreceptors can be used successfully with toners, such as liquid toners, to produce high quality images. The high quality of the imaging system can be maintained after repeated cycling.

Other features and advantages of the invention will be apparent from the following description of the particular embodiments thereof, and from the claims.

DETAILED DESCRIPTION OF PREFERRED EMBODIMENTS

An organophotoreceptor as described herein has an electrically conductive substrate and a photoconductive element including a charge generating compound and a bridged charge transport material having two aromatic groups, $Y_1$ and $Y_2$, bonded together through a bridging group including a central sulfur atom linkage, linking groups $X_1$ and $X_2$, $Z_1$ and $Z_2$ groups, and $W_1$ and $W_2$ groups, where $Z_1$ and $Z_2$ comprise, each independently, a bond, a vinyl group, a —$CR_1$=N—$NR_2$— group, or a —$CR_3$=N—N=$CR_4$— group where $R_1$, $R_2$, $R_3$, and $R_4$ comprise, each independently, H, an alkyl group, an alkenyl group, an alkynyl group, an acyl group, an aromatic group, or a heterocyclic group; $X_1$ and $X_2$ are, each independently, a linking group, such as a —$(CH_2)_m$— group, where m is an integer between 1 and 10, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkenyl group, an alkynyl group, an acyl group, a heterocyclic group, an aromatic group, or a part of a ring group, such as cycloalkyl groups, heterocyclic groups, or a benzo group; and $W_1$ and $W_2$ are, each independently, a —$(CH_2)_n$— group or a —$(CH_2)_{n-1}$—C(=O)— group, where n is an integer between 1 and 10, inclusive.

These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted)arylamines such as triaryl amines, polyvinyl carbazole, polyvinyl pyrene, polyacenaphthylene, and the charge transport compounds described in U.S. Pat. Nos. 6,689,523, 6,670,085, and 6,696,209, and U.S. patent application Ser. Nos. 10/431,135, 10/431,138, 10/699,364, 10/663,278, 10/699,581, 10/449,554, 10/748,496, 10/789,094, 10/644,547, 10/749,174, 10/749,171, 10/749,418, 10/699,039, 10/695,581, 10/692,389, 10/634,164, 10/663,970, 10/749,164, 10/772,068, 10/749,178, 10/758,869, 10/695,044, 10/772,069, 10/789,184, 10/789,077, 10/775,429, 10/775,429, 10/670,483, 10/671,255, 10/663,971, 10/760,039. All the above patents and patent applications are incorporated herein by reference.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8- trinitrothioxanthone, 2,6,8-trinitro-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene) malonate, anthraquinodimethane derivatives such as 11,11, 12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluoroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinodimethane, 2,4,5,7-tetranitro-9-fluorenone, 2,4,7-trinitro-9-dicyanomethylene fluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232,800, 4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport material having the formula:

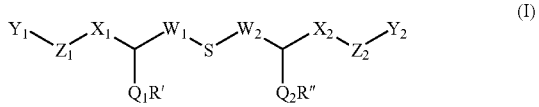 (I)

where $Z_1$ and $Z_2$ comprise, each independently, a bond, a vinyl group, a —$CR_1$=N—$NR_2$— group, or a —$CR_3$=N—N=$CR_4$— group where $R_1$, $R_2$, $R_3$, and $R_4$ comprise, each independently, H, an alkyl group, an alkenyl group, an alkynyl group, an acyl group, an aromatic group, or a heterocyclic group;

$Y_1$ and $Y_2$ comprise, each independently, an aromatic group;

$X_1$ and $X_2$ are, each independently, a linking group, such as a —$(CH_2)_m$— group, where m is an integer between 1 and 10, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkylsulfanyl group, an alkenyl group, an alkynyl group, an acyl group, a heterocyclic group, an aromatic group, or a part of a ring group, such as cycloalkyl groups, heterocyclic groups, or a benzo group;

$W_1$ and $W_2$ are, each independently, a —$(CH_2)_n$— group or a —$(CH_2)_n$-1-C(=O)— group, where n is an integer between 1 and 10, inclusive;

$Q_1$ and $Q_2$ are, each independently, O, S, or NR; and

R, R', and R" are, each independently, H, an alkyl group, an alkenyl group, an alkynyl group, an acyl group, a heterocyclic group, or an aromatic group.

A heterocyclic group includes any monocyclic or polycyclic (e.g., bicyclic, tricyclic, etc.) ring compound having at least a heteroatom (e.g., O, S, N, P, B, Si, etc.) in the ring.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4) dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, the linking group may comprise at least one heteroatom such as O, S, Si, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or by a linking group (as in stilbenyl, diphenyl sulfone, an arylamine group). The linking group may include an aliphatic group, an aromatic group, a heterocyclic group, or a combination thereof. Furthermore, the linking group may comprise at least one heteroatom such as O, S, Si, and N.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, alkenyl group, alkynyl group, phenyl group, aromatic group, heterocyclic group, arylamine group, julolidine group, carbazole group, (N,N-disubstituted)arylamine group, etc.) may have any substituent thereon which is consistent with the bond structure of that group. For example, where the term 'alkyl group' or 'alkenyl group' is used, that term would not only include unsubstituted linear, branched and cyclic alkyl group or alkenyl group, such as methyl, ethyl, ethenyl or vinyl, isopropyl, tert-butyl, cyclohexyl, cyclohexenyl, dodecyl and the like, but also substituents having heteroatom(s), such as 3-ethoxylpropyl, 4-(N,N-diethylamino)butyl, 3-hydroxypentyl, 2-thiolhexyl, 1,2,3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N,N-disubstituted)aminophenyl, 2,4-dihydroxyphenyl, 2,4,6-trithiophenyl, 2,4,6-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (Tedlar®, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodine, conductive polymers such as polypyrroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers (such as a dye or pigment). Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazopigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as TINUVIN® 144 and TINUVIN® 292 (from Ciba Specialty Chemicals, Terrytown, N.Y.), hindered alkoxydialkylamines such as TINUVIN® 123 (from Ciba Specialty Chemicals), benzotriazoles such as Tinuvan 328, TINUVIN® 900 and TINUVIN® 928 (from Ciba Specialty Chemicals), benzophenones such as SANDUVOR® 3041 (from Clariant Corp., Charlotte, N.C.), nickel compounds such as ARBESTAB™ (from Robinson Brothers Ltd, West Midlands, Great Britain), salicylates, cyanocinnamates, benzylidene malonates, benzoates, oxanilides such as SANDUVOR® VSU (from Clariant Corp., Charlotte, N.C.), triazines such as Cyagard UV-1164 (from Cytec Industries Inc., N.J.), polymeric sterically hindered amines such as LUCHEM™ (from Atochem North America, Buffalo, N.Y.). In some embodiments, the light stabilizer is selected from the group consisting of hindered trialkylamines having the following formula:

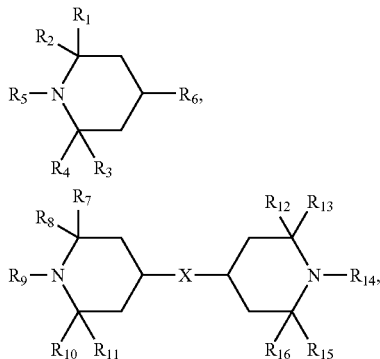

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. IUPILON®-A from Mitsubishi Engineering Plastics, or LEXAN® 145 from General Electric); polycarbonate Z which is derived from cyclohexylidene bisphenol (e.g. IUPILON®-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET® TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics, and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

As described herein, an organophotoreceptor comprises a charge transport material having the formula

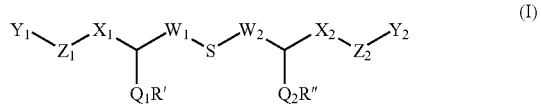

(I)

where $Z_1$ and $Z_2$ comprise, each independently, a bond, a vinyl group, a —$CR_1$=N—$NR_2$— group, or a —$CR_3$=N—N=$CR_4$— group where $R_1$, $R_2$, $R_3$, and $R_4$ comprise, each independently, H, an alkyl group, an alkenyl group, an alkynyl group, an acyl group, an aromatic group, or a heterocyclic group;

$Y_1$ and $Y_2$ comprise, each independently, an aromatic group;

$X_1$ and $X_2$ are, each independently, a linking group, such as a —$(CH_2)_m$— group, where m is an integer between 1 and 10, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_e$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkylsulfanyl group, an alkenyl group, an alkynyl group, an acyl group, a heterocyclic group, an aromatic group, or a part of a ring group, such as cycloalkyl groups, heterocyclic groups, or a benzo group;

$W_1$ and $W_2$ are, each independently, a —$(CH_2)_n$— group or a —$(CH_2)_{n-1}$—C(=O)— group, where n is an integer between 1 and 10, inclusive;

$Q_1$ and $Q_2$ are, each independently, O, S, or NR; and

R, R', and R" are, each independently, H, an alkyl group, an alkenyl group, an alkynyl group, an acyl group, a heterocyclic group, or an aromatic group.

With respect to Formula (I), substitution is liberally allowed, especially on $W_1$, $W_2$, $X_1$, $X_2$, $Y_1$, $Y_2$, $Z_1$, and $Z_2$. Variation of the substituents, such as an aromatic group, an alkyl group, a heterocyclic group, and a ring group such as a benzo group, on $W_1$, $W_2$, $X_1$, $X_2$, $Y_1$, $Y_2$, $Z_1$, and $Z_2$ can result in various physical effects on the properties of the compounds, such as mobility, solubility, compatibility, stability, spectral absorbance, dispersibility, and the like, including, for example, substitutions known in the art to effect particular modifications.

The charge transport material of Formula (I) may be symmetrical or unsymmetrical. Thus, for example, $X_1$ and $X_2$ may be the same or different. Similarly, $Y_1$ and $Y_2$ may be the same or different; $Z_1$ and $Z_2$ may be the same or different $R_1$ and $R_2$ may be the same or different; $R_7$ and $R_8$ may be the same or different; or $R_3$, $R_4$, $R_5$, and $R_6$ may be the same or different. In addition, Formula (I) for the charge transport material is intended to cover isomers.

The organophotoreceptors as described herein may comprise an improved charge transport material of Formula (I) where $Y_1$ and $Y_2$ comprise, each independently, an aryl group, such as a phenyl group, a naphthyl group, a bis[(N,N-disubstituted)amino]aryl group, a julolidinyl group, an (N-substituted)arylamine group, and an (N,N-disubstituted) arylamine group, or an aromatic heterocyclic group, such as a furanyl group, a thiophenyl group, a pyrrolyl group, an indolyl group, a carbazolyl group, a benzofuranyl group, a benzothiophenyl group, a dibenzofuranyl group, a dibenzothiophenyl group, a pyridinyl group, a pyridazinyl group, a pyrimidinyl group, a pyrazinyl group, a triazinyl group, a tetrazinyl group, a pentazinyl group, a quinolinyl group, an isoquinolinyl group, a cinnolinyl group, a phthalazinyl group, a quinazolinyl group, a quinoxalinyl group, a naphthyridinyl group, an acridinyl group, a phenanthridinyl group, a phenanthrolinyl group, an anthyridinyl group, a purinyl group, a pteridinyl group, an alloxazinyl group, a phenazinyl group, a phenothiazinyl group, a phenoxazinyl group, a phenoxathiinyl group, a dibenzo(1,4)dioxinyl group, a thianthrenyl group, a bicarbazolyl group, and a 1,6-di(10H-10-phenothiazinyl)hexyl group. The aryl group or the aromatic heterocyclic group may include at least a substituent selected from the group consisting of an alkyl group, an alkenyl group such as a vinyl group, an alkynyl group, an acyl group, an aromatic group, a heterocyclic group, an amino group, an (N,N-disubstituted)hydrazone group, an enamine group, an azine group, an epoxy group, a thiiranyl group, and an aziridinyl group.

In some embodiments of interest, $Y_1$ and $Y_2$, each independently, is selected from the group consisting of the following formulae:

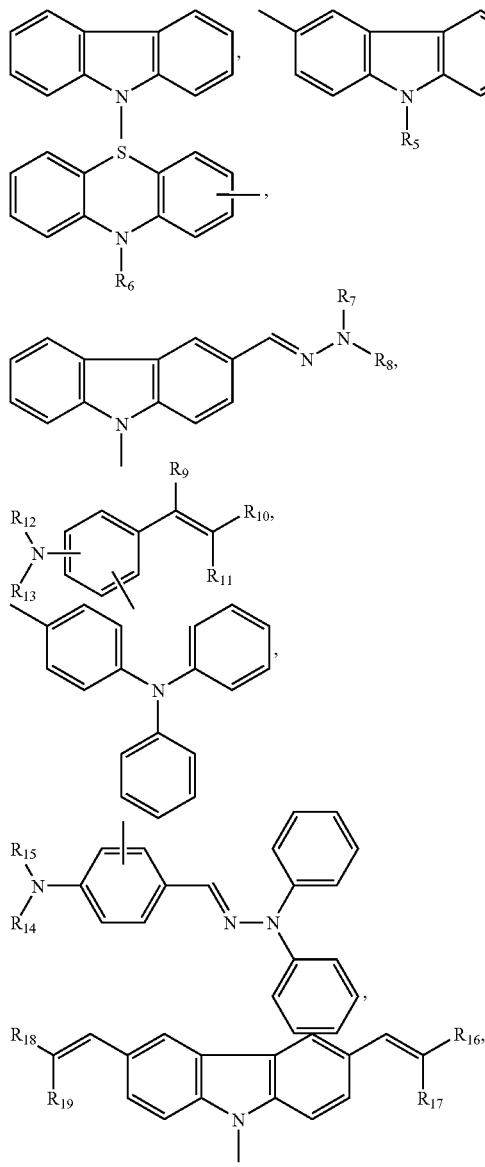

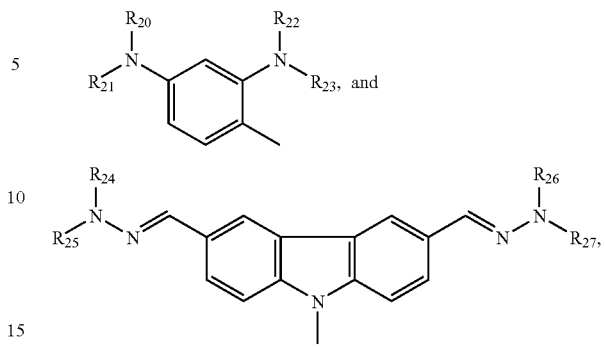

where $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ comprise, each independently, H, an alkyl group, an alkenyl group, an alkynyl group, an acyl group, an aromatic group, or a heterocyclic group. The above $Y_1$ and $Y_2$ groups may further include at least a substituent, such as an alkyl group, an alkenyl group, such as a vinyl group, an allyl group, and a 2-phenylethenyl group, an alkynyl group, an acyl group, an aromatic group, a heterocyclic group, an (N,N-disubstituted) hydrazone group, an enamine group, and an azine group.

In other embodiments of interest, $X_1$ and $X_2$ are, each independently, a —$CH_2$— group, a —$OCH_2$— group, or a —Ar—$OCH_2$— group; and $W_1$ and $W_2$ are, each independently, a bond, a —$CH_2$— group, a —$CH_2CH_2$— group, or a —$(CH_2)_{n-1}$—$C(=O)$— group, where n is an integer between 2 and 6 and Ar comprises an aromatic group. $Z_1$ and $Z_2$ may comprise, each independently, a bond or a —CR=N—$NR_2$— group where $R_1$ is H and $R_2$ comprises an aromatic group.

In further embodiments of interest, $Z_1$ and $Z_2$ comprise, each independently, a —$CR_3$=N—N=$CR_4$— group; and $X_1$ and $X_2$ are, each independently, a —Ar—$OCH_2$—group, where Ar comprises an aromatic group and $R_3$ and $R_4$ comprise, each independently, H, an alkyl group, an aromatic group, or a heterocyclic group.

Specific, non-limiting examples of suitable charge transport materials within Formula (I) of the present invention have the following structures:

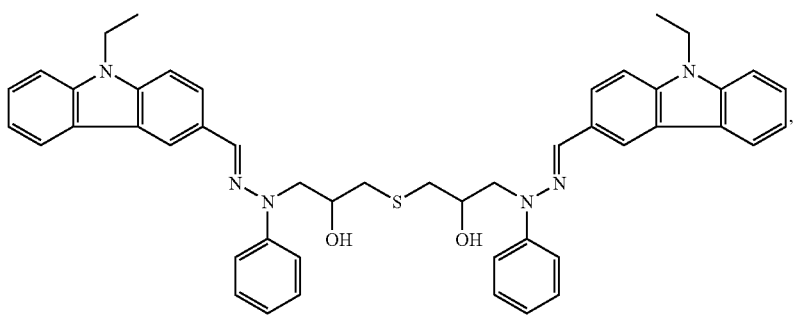

(1)

(2)
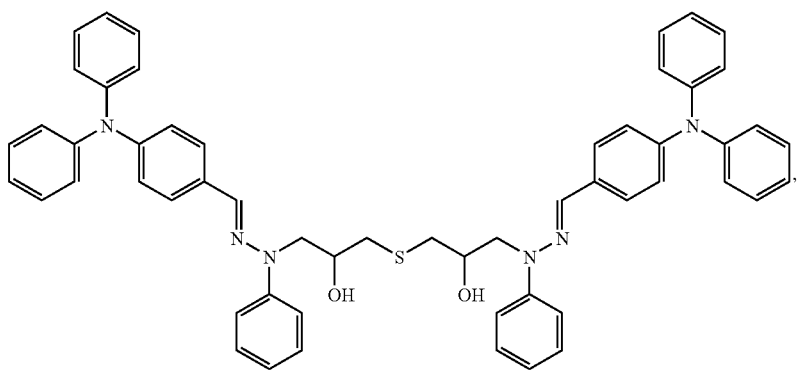
(3)
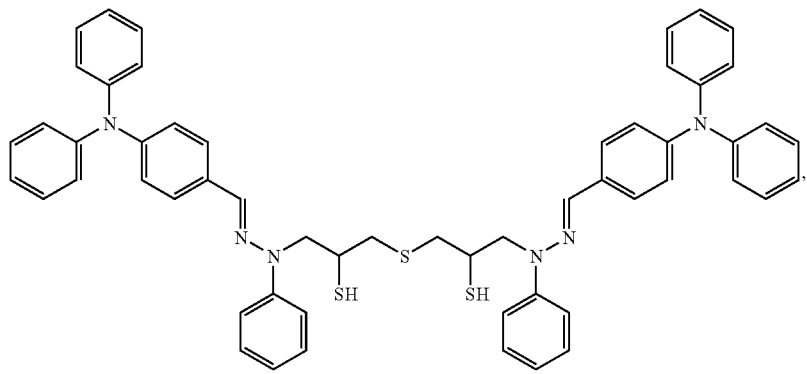
(4)
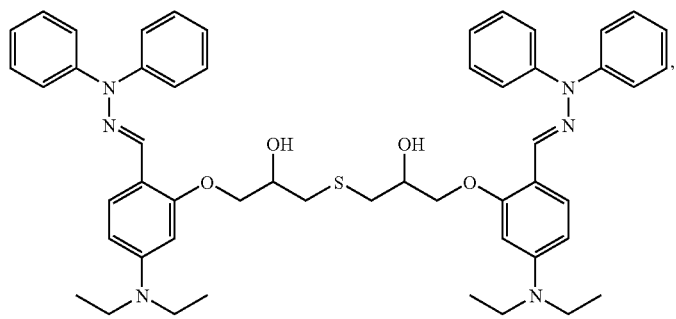
(5)
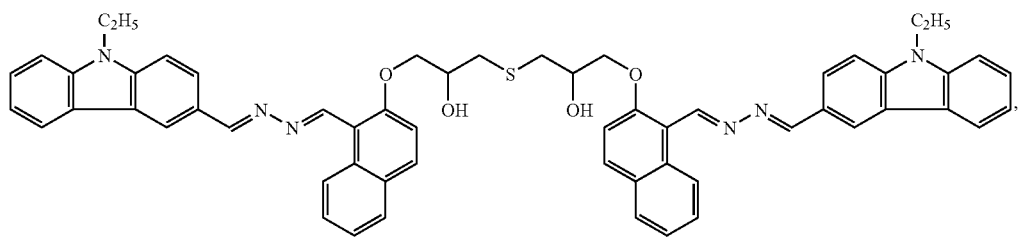

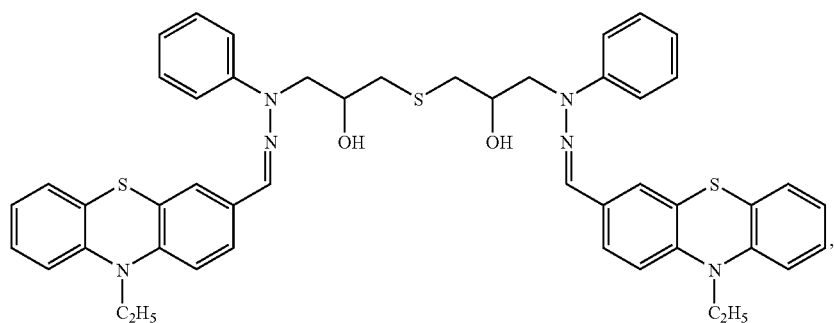
(6)
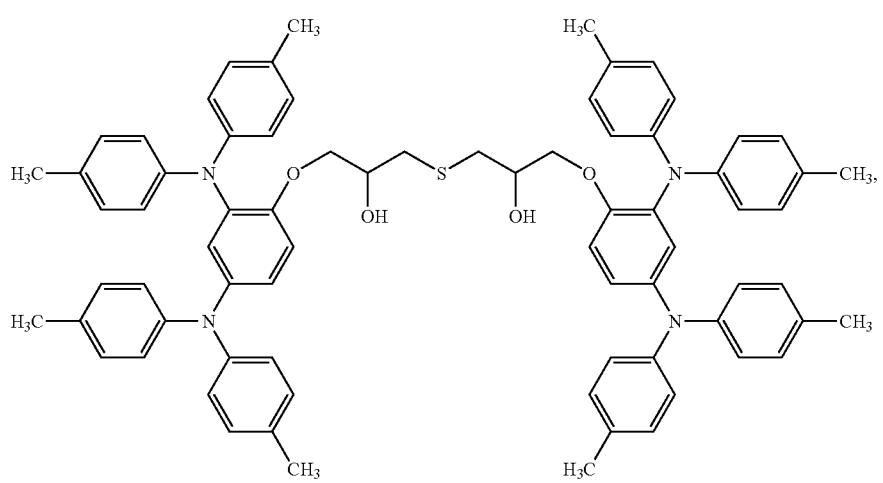
(7)
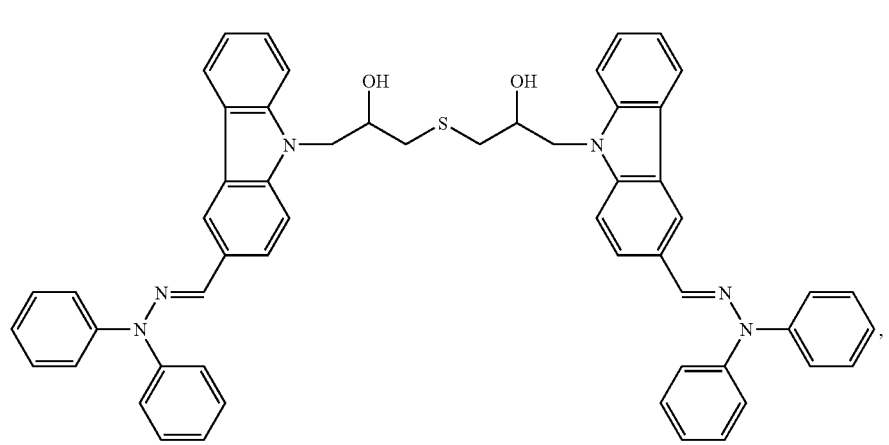
(8)

(9)

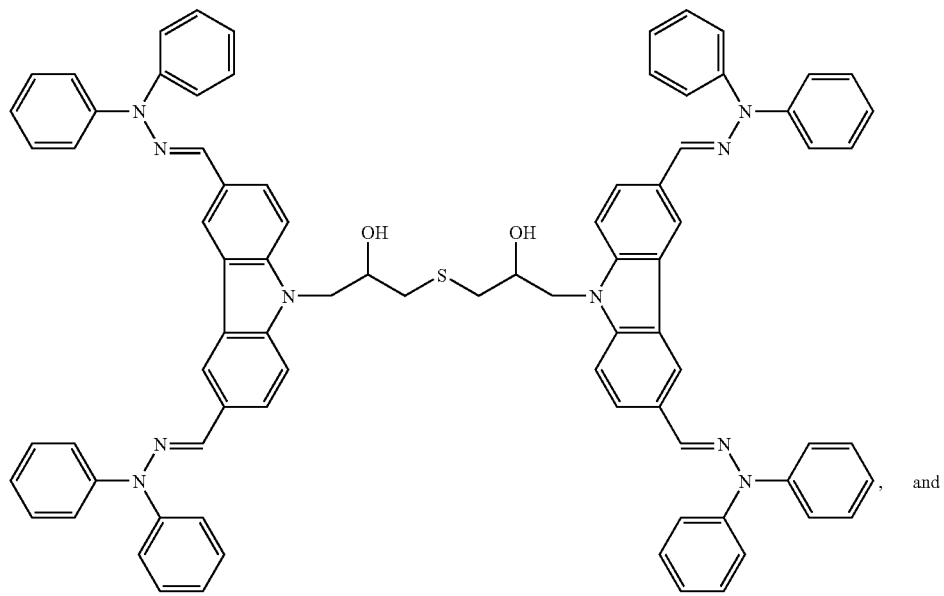

, and (10)

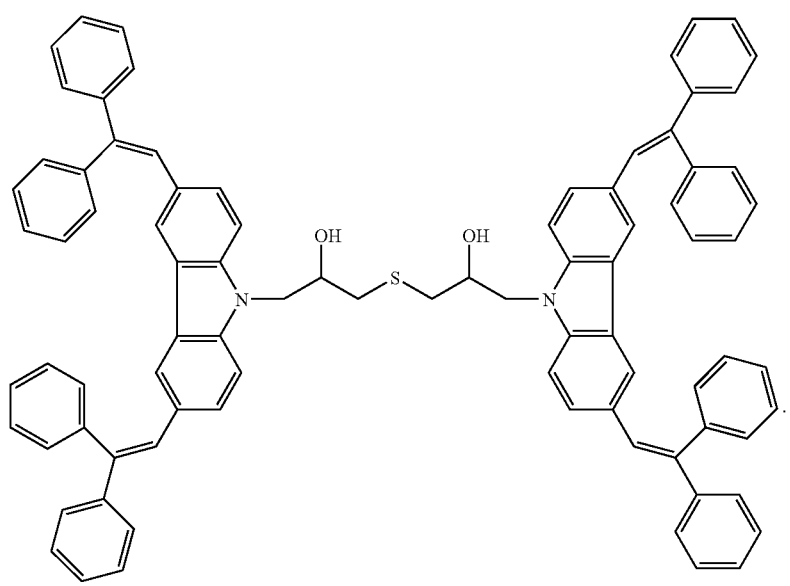

.

Synthesis Of Charge Transport Materials

The synthesis of the charge transport materials of this invention can be prepared by the following multi-step synthetic procedures, although other suitable procedures can be used by a person of ordinary skill in the art based on the disclosure herein.

General Synthetic Procedure for Charge Transport Materials of Formula (I)

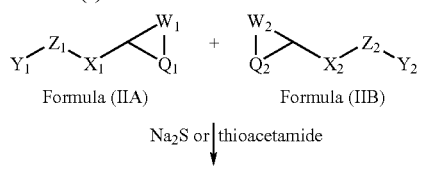

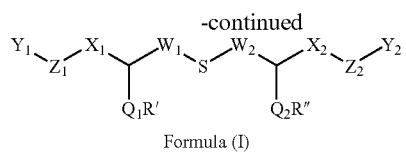

Formula (I)

The charge transport materials of Formula (I) may be prepared by reacting at least an aromatic compound having a reactive ring group (e.g., the ring including $W_1$—$Q_1$ or the ring including $W_2$—$Q_2$) with a bridging compound selected from the group consisting of sodium sulfide and thioacetamide. The reactive ring group may be selected from the group consisting of heterocyclic ring groups which have a higher strain energy than its corresponding open-ring structure. The conventional definition of strain energy is that it represents the difference in energy between the actual molecule and a completely strain-free molecule of the same constitution. More information about the origin of strain energy can be found in the article by Wiberg et al., "A Theoretical Analysis of Hydrocarbon Properties: II Additivity of Group Properties and the Origin of Strain Energy," J. Am. Chem. Soc. 109, 985 (1987). The above article is incorporated herein by reference. The heterocyclic ring group may have 3, 4, 5, 7, 8, 9, 10, 11, or 12 members, in further embodiments 3, 4, 5, 7, or 8 members, in some embodiments 3, 4, or 8 members, and in additional embodiments 3 or 4 members. Non-limiting examples of such heterocyclic ring are cyclic ethers (e.g., epoxides and oxetane), cyclic amines (e.g., aziridine), cyclic sulfides (e.g., thiirane), cyclic amides (e.g., 2-azetidinone, 2-pyrrolidone, 2-piperidone, caprolactam, enantholactam, and capryllactam), N-carboxy-α-amino acid anhydrides, lactones, and cyclosiloxanes. The chemistry of the above heterocyclic rings is described in George Odian, "Principle of Polymerization," second edition, Chapter 7, p. 508-552 (1981), incorporated herein by reference.

The preparations of some aromatic compounds having Formula (IIA) and/or (IIB) have been disclosed in U.S. patent application Ser. Nos. 10/749,178, 10/695,581, 10/692,389, 10/634,164, 10/663,970, 10/749,164, 10/772,068, 10/749,269, and 10/758,869, all of which are incorporated herein by reference. In general, the aromatic compound having a reactive ring group may be prepared by the reaction of the corresponding aromatic compound having a hydroxyl group, thiol group, a carboxyl group, a primary amino group, or a secondary amine group with an organic halide having a reactive ring group.

In some embodiments of interest, the reactive ring group is an epoxy group where $W_1$ (or $W_2$) is a —$CH_2$— group and $Q_1$ (or $Q_2$) is O. An aromatic compound having an epoxy group may be prepared by reacting a corresponding aromatic compound with an organic halide comprising an epoxy group. Non-limiting examples of suitable organic halide comprising an epoxy group as the reactive ring group are epihalohydrins, such as epichlorohydrin. The organic halide comprising an epoxy group can also be prepared by the epoxidation reaction of the corresponding alkene having a halide group. Such epoxidation reaction is described in Carey et al., "Advanced Organic Chemistry, Part B: Reactions and Synthesis," New York, 1983, pp. 494-498, incorporated herein by reference. The alkene having a halide group can be prepared by the Wittig reaction between a suitable aldehyde or keto compound and a suitable Wittig reagent. The Wittig and related reactions are described in Carey et al., "Advanced Organic Chemistry, Part B: Reactions and Synthesis," New York, 1983, pp. 69-77, which is incorporated herein by reference.

In other embodiments of interest, the reactive ring group is a thiiranyl group where $W_1$ (or $W_2$) is a —$CH_2$— group and $Q_1$ (or $Q_2$) is S. An aromatic compound having an epoxy group, such as those described above, can be converted into the corresponding thiiranyl compound by refluxing the epoxy compound and ammonium thiocyanate in tetrahydrofuran. Alternatively, the corresponding thiiranyl compound may be obtained by passing a solution of the above-described epoxy compound through 3-(thiocyano)propyl-functionalized silica gel (commercially available form Aldrich, Milwaukee, Wis.). Alternatively, a thiiranyl compound may be obtained by the thia-Payne rearrangement of a corresponding epoxy compound. The thia-Payne rearrangement is described in Rayner, C. M. Synlett 1997, 11; Liu, Q. Y.; Marchington, A. P.; Rayner, C. M. Tetrahedron 1997, 53, 15729; Ibuka, T. Chem. Soc. Rev. 1998, 27, 145; and Rayner, C. M. Contemporary Organic Synthesis 1996, 3, 499. All the above four articles are incorporated herein by reference.

In other embodiments of interest, the reactive ring group is an aziridinyl group where $W_1$ (or $W_2$) is a —$CH_2$— group and $Q_1$ (or $Q_2$) is NR. An aziridine compound may be obtained by the aza-Payne rearrangement of a corresponding aromatic compounds having an epoxy group, such as one of those epoxy compounds described above. The thia-Payne rearrangement is described in Rayner, C. M. Synlett 1997, 11; Liu, Q. Y.; Marchington, A. P.; Rayner, C. M. Tetrahedron 1997, 53, 15729; and Ibuka, T. Chem. Soc. Rev. 1998, 27, 145. All the above three articles are incorporated herein by reference. Alternatively, an aziridine compound may be prepared by the addition reaction between a suitable nitrene compound and a suitable alkene. Such addition reaction is described in Carey et al., "Advanced Organic Chemistry, Part B: Reactions and Synthesis," New York, 1983, pp. 446-448, incorporated herein by reference.

In further embodiments of interest, the reactive ring group is an oxetanyl group where $W_1$ (or $W_2$) is a —$CH_2CH_2$— group and $Q_1$ (or $Q_2$) is O. An oxetane compound may be prepared by the Paterno-Buchi reaction between a suitable carbonyl compound and a suitable alkene. The Paterno-Buchi reaction is described in Carey et al., "Advanced Organic Chemistry, Part B: Reactions and Synthesis," New York, 1983, pp. 335-336, incorporated herein by reference.

In additional examples, the reactive ring may be a 5 or 7-membered ring comprising a —COO— group or a —CONR— group, such as butyrolactone, N-methylbutyrolactam, N-methylcaprolactam, and caprolactone.

When a symmetrical charge transport material of Formula (I) is desired, the aromatic compound having Formula (IIA) should be the same as the aromatic compound having Formula (IIB). In the other words, a symmetrical charge transport material may be obtained when $Y_1$ and $Y_2$ are the same, $Z_1$ and $Z_2$ are the same, $X_1$ and $X_2$ are the same, $W_1$ and $W_2$ are the same, and $Q_1$ and $Q_2$ are the same. To prepare a symmetrical charge transport material of Formula (I), either sodium sulfide or thioacetamide may react with an aromatic compound having Formula (IIA) or (IIB) in a molar ratio of at least 1:2. Optionally, an excess of the aromatic compound having Formula (IIA) or (IIB) may be used to maximize the desirable symmetrical charge transport material of Formula (I).

When an unsymmetrical charge transport material of Formula (I) is desired, the aromatic compound having Formula (IIA) should be different from the aromatic compound having Formula (IIB). In the other words, an unsymmetrical charge transport material may be obtained when $Y_1$ and $Y_2$ are different, $Z_1$ and $Z_2$ are different, $X_1$ and $X_2$ are different, $W_1$ and $W_2$ are different, or $Q_1$ and $Q_2$ are different. To prepare an unsymmetrical charge transport material of Formula (I), a bridging compound may react with two different arylamine hydrazone compounds in two sequential reactions. In the first reaction, either sodium sulfide or thioacetamide may react with a first aromatic compound. Optionally, an excess of either sodium sulfide or thioacetamide may be used to maximize the desirable product and to minimize the undesirable symmetrical side product. In the second reaction, the product obtained in the first reaction may react with a second aromatic compound to form the desirable unsymmetrical charge transport material of Formula (I).

The desired product, either symmetrical or unsymmetrical, may be isolated and purified by conventional purification techniques such as column chromatography, preparative thin layer chromatography, and recrystallization.

The ring-opening reaction between either sodium sulfide or thioacetamide and the the ring including $W_1$—$Q_1$ produces a group comprising a S atom attached to the $W_1$—CH-$Q_1R'$ group where R' is H; and the ring-opening reaction between the same sodium sulfide or thioacetamide and the ring including $W_2$—$Q_2$ produces a group comprising the same S atom attached to a —$W_2$—CH—$Q_2R''$ group where R" is H. The hydrogens in $Q_1H$ or/and $Q_2H$ may be further converted into an alkyl group, an alkenyl group, an alkynyl group, an acyl group, a heterocyclic group, or an aromatic group by known substitution reactions such as alkylation reaction and acylation reaction.

The preparation of the charge transport material of Formula (I) may be carried out by refluxing the corresponding aromatic compound having Formula (IIA) and/or (IIB) with sodium sulfide in a solvent, such as butanone, acetone, THF, or dioxane, in the presence of water. The amount of water may vary depending on the amount of sodium sulfide used. The minimum amount of water should be added to cause the sodium sulfide to dissolve.

Alternatively, the charge transport material of Formula (I) may be prepared by refluxing the corresponding aromatic compound having Formula (IIA) and/or (IIB) with thioacetamide in a solvent, such as butanone, acetone, THF, or dioxane. The amount of the base may vary from 5% to 12% by weight. The product can be purified by column chromatography and/or recrystallization.

The invention will now be described further by way of the following examples.

EXAMPLES

Example 1

Synthesis And Characterization Charge Transport Materials

This example describes the synthesis and characterization of Compounds (1)-(10) in which the numbers refer to formula numbers above. The characterization involves chemical characterization of the compounds. The electrostatic characterization, such as mobility and ionization potential, of the materials formed with the compounds is presented in a subsequent example.

Compound (1) by Procedure A

9-Ethyl-3-Carbazolecarboxaldehyde N-(2,3-Epoxypropyl)-N-Phenylhydrazone. A mixture of potassium hydroxide powder (KOH, 85%, 198 g, 3 mol,) and anhydrous sodium sulfate ($Na_2SO_4$, 51 g, 0.369 mol) was added in three stages to a mixture of 9-ethyl-3-carbazolecarboxaldehyde N-phenylhydrazone (313.4 g, 1 mol) and epichlorohydrin (1.5 mol), while keeping the reaction mixture at 20-25° C. In the first stage, 33 g of $Na_2SO_4$ and 66 g of KOH were added initially. In the second stage, 9.9 g of $Na_2SO_4$ and 66 g of KOH were added 1 hour into the reaction. In the third stage, 9.9 g of $Na_2SO_4$ and 66 g of KOH were added 2 hours into the reaction. The reaction mixture was stirred vigorously at 35-40° C. until the starting hydrazone disappeared (approximately 3-4 hours). Subsequently, the mixture was cooled to room temperature and any remaining solids were removed by filtration. The liquid organic phase was treated with diethyl ether and washed with distilled water until the washed water had a neutral pH. The organic layer was dried over anhydrous magnesium sulfate, treated with activated charcoal, and filtered. The solvent and excess epichlorohydrin were removed by evaporation in a rotary evaporator. The residue was recrystallized from a mixture of toluene and 2-propanol in a 1:1 volume ratio. The crystals formed upon standing were filtered off and washed with 2-propanol to give 290 g of product (78.5% yield). The melting point of the product was found to be 136-137° C. (recrystallized from toluene). The $^1$H-NMR spectrum (250 MHz) of the product in $CDCl_3$ was characterized by the following chemical shifts (δ, ppm): 8.35 (s, 1H, 4-$H_{Ht}$); 8.14 (d, J=7.8 Hz, 1H, 1-$H_{Ht}$); 7.93 (d, J=7.6 Hz, 1H, 2-$H_{Ht}$); 7.90 (s, 1H, CH=N); 7.54-7.20 (m, 8H, Ph, Ht); 6.96 (t, J=7.2 Hz, 1H, 4-$H_{Ph}$); 4.37 (m, 3H, C$\underline{H}_2$CH$_3$, one of the NCH$_2$ protons); 4.04 (dd, $J_1$=4.3 Hz, $J_2$=16.4 Hz, 1H, next of the NCH$_2$ protons); 3.32 (m, 1H, CH); 2.88 (dd, 1H, part of the ABX system, cis-$H_A$ of CH$_2$O, $J_{AX}$=2.6 Hz, $J_{AB}$=4.9 Hz); 2.69 (dd, 1H, part of the ABX system, trans-$H_B$ of CH$_2$O, $J_{BX}$=4.0 Hz); and 1.44 (t, J=7.2 Hz, 3H, CH$_3$). An elemental analysis yielded the following results in weight percent C 78.32, H 6.41, and N 11.55, which compared with calculated values for $C_{24}H_{23}N_3O$ in weight percent of C 78.02, H 6.28, and N 11.37.

Procedure A

A mixture of 9-ethyl-3-carbazolecarboxaldehyde N-(2,3-epoxypropyl)-N-phenyl hydrazone (3.1 g, 8.39 mmol,) dissolved in 5 ml of butanone and sodium sulfide (0.52 g, 4.0 mmol, from Fluka, 60-62%) dissolved in 0.5 ml water was added to a 25 ml 2-neck round bottom flask equipped with a reflux condenser and a magnetic stirrer. The mixture was refluxed for 3 hours. After the completion of the reaction, as indicated by thin layer chromatography, the reaction mixture was extracted with chloroform which was then distilled off to yield an oily residue. The oily residue was purified by column chromatography using a column packed with silica gel (grade 62, 60-200 mesh, 150 Å, commercially obtained from Aldrich, Milwaukee, Wis.) and a mixture of acetone and hexane in a volume ratio of 1:4 as the eluant. Fractions containing the product were collected and the solvent was evaporated to yield 1.3 g (40.2%) of Compound (1). Compound (1) was recrystallized from a mixture of 1,4-dioxane and 2-propanol in a volume ratio of 2:1. The melting point of Compound (1) was found to be 194.5-195.9° C. The infrared absorption spectrum of Compound (1) was characterized by the following absorptions (KBr window, cm$^{-1}$): 3550-3200 (OH, broad); 3047 (aromatic CH); 2982, 2954, 2915 (aliphatic CH); and 745 (CH=CH of 3-substituted carbazole). The $^1$H-NMR spectrum (100 MHz) of Compound (1) in DMSO-$d_6$ was characterized by the following chemical shifts (δ, ppm): 8.39 (s, 2H, 4-H Ht); 8.30-8.05 (m, 4H, 1-H Ht, CH=N); 8.05-7.80 (m, 2H, 2-H Ht); 7.75-7.05 (m, 16H, Ht, Ph); 7.05-6.70 (m, 2H, 4-H Ph); 5.41 (m, 2H, OH); 4.60-3.80 (m, 10H, C$\underline{H}_2$CH$_3$, NCH$_2$CH); 3.15-2.80 (m, 4H, CH$_2$S); and 1.29 (t, 6H, J=7.5 Hz, CH$_3$). An elemental analysis yielded the following results in weight percent: C, 74.38; H, 6.16; N, 10.97, which compared with calculated values for $C_{48}H_{48}N_6O_2S$ in weight percent of: C, 74.58; H, 6.26; N, 10.87.

Compound (1) by Procedure B

Compound (1) was also prepared according to Procedure A for Compound (1) above except that, for Procedure B, sodium sulfide hydrate was replaced by a mixture of thioacetamide (0.286 g, 3.81 mmol, from Aldrich, Milwaukee, Wis.) and 0.5 ml of triethylamine. The reaction time was 2 hours. The yield was 2.4 g (74.07%). The melting point of the product was found to be 195-196° C. The IR and $^1$H NMR spectra of the product are identical to those of Compound (1) from Procedure A.

Compound (2) by Procedure C 4-(Diphenylamino)benzaldehyde N-(2,3-Epoxypropyl)-N-Phenylhydrazone. A mixture of phenylhydrazine (0.1 mole, from Aldrich, Milwaukee, Wis.) and 4-(diphenylamino)benzaldehyde (0.1 mole, from Fluka, Buchs SG, Switzerland) was dissolved in 100 ml of isopropanol in a 250 ml 3-neck round bottom flask equipped with a reflux condenser and a mechanical stirrer. The solution was refluxed for 2 hours. At the end of the reaction, as indicated by thin layer chromatography the disappearance of the starting materials, the mixture was cooled to room temperature. The 4-(diphenylamino)benzaldehyde phenylhydrazone crystals that formed upon standing were filtered off, washed with isopropanol, and dried in a vacuum oven at 50° C. for 6 hours.

A mixture of 4-(diphenylamino)benzaldehyde phenylhydrazone (3.6 g, 0.01 mole), 85% powdered potassium hydroxide (2.0 g, 0.03 mole) and anhydrous potassium carbonate (0.7 g, 0.005 mole) in epichlorohydrin (25 ml) was stirred vigorously at 55-60° C. for 1.5-2 hours. The course of the reaction was monitored by thin layer chromatography using silica gel 60 F254 plates (from Merck, Whitehouse Station, N.J.) using a mixture of acetone and hexane in a volume ratio of 1:4 as eluant. After the termination of the reaction, the mixture was cooled to room temperature, diluted with ether, and washed with water until the washed water reached a neutral pH. The organic phase was dried over anhydrous magnesium sulfate, treated with activated charcoal, and filtered. Ether was removed from the organic phase and the residue was dissolved in a mixture of toluene and isopropanol in a volume ratio of 1:1. The crystals that formed upon standing were filtered off and washed with isopropanol to yield 3.0 g (71.4%) of the product, 4-(diphenylamino)benzaldehyde N-(2,3-epoxypropyl)-N-phenylhydrazone. The product was recrystallized for a second time from a mixture of toluene and isopropanol in a volume ratio of 1:1. The melting point of the recrystallized product was found to be 141-142.5° C. The $^1$H-NMR spectrum (250 MHz) of the product in CDCl$_3$ was characterized by the following chemical shifts (δ, ppm): 7.65-6.98 (m, 19H), 6.93 (t, J=7.2 Hz, 1H), 4.35 (dd, 1H), 3.99 (dd, 1H), 3.26 (m, 1H), 2.84 (dd, 1H), and 2.62 (dd, 1H). An elemental analysis yielded the following results in weight percent: C 80.02, H 6.31, and N 9.91, which compares with calculated values for $C_{28}H_{25}N_3O$ in weight percent: C 80.16, H 6.01, and N 10.02.

Procedure C

Compound (2) was prepared according to Procedure A for Compound (1) above except that, in Procedure C, 9-ethyl-3-carbazolecarboxaldehyde N-(2,3-epoxypropyl)-N-phenylhydrazone was replaced by 4-(diphenylamino)benzaldehyde N-(2,3-epoxypropyl)-N-phenylhydrazone (3.1 g, 7.39 mmol) and the amount of sodium sulfide reduced to (0.46 g, 3.52 mmol). The reaction time was 3 hours. The product obtained after purification by column chromatography was recrystallized from toluene. The yield of Compound (2) was 1.34 g (41.5%). The melting point of Compound (2) was found to be 154.5-156° C. The infrared absorption spectrum of Compound (2) was characterized by the following absorptions (KBr window, cm$^{-1}$): 3600-3130 (OH, broad); 3060, 3035 (aromatic CH); 2913 (aliphatic CH); 751, 695 (CH=CH of monosubstituted benzene); and 834 (CH=CH of 1,4-disubstituted benzene). The $^1$H-NMR spectrum (100 MHz) of Compound (2) in CDCl$_3$ was characterized by the following chemical shifts (δ, ppm): 7.59 (s, 2H, CH=N); 7.06-6.82 (m, 38H, Ar); 4.45-4.20 (m, 2H, NCH$_2$CH); 4.20-3.86 (m, 4H, NCH$_2$); 3.70-3.46 (m, 2H, OH); and 3.00-2.70 (m, 4H CH$_2$S). An elemental analysis yielded the following results in weight percent: C, 76.88; H, 5.86; N, 9.87, which compared with calculated values for $C_{56}H_{52}N_6O_2S$ in weight percent of: C, 77.03; H, 6.00; N, 9.63.

Compound (2) by Procedure D

Compound (2) was also prepared according to Procedure C for Compound (2) above except that, in Procedure D, sodium sulfide was replaced by a mixture of thioacetamide (0.27 g, 3.36 mmol, from Aldrich, Milwaukee, Wis.) and 0.5 ml of triethylamine. The reaction time was 2 hours. The yield was 2.26 g (70.3%). The melting point of the product was found to be 154-155° C. A sample of this product was combined with a sample of Compound (2) by Procedure C and the mixture did not exhibit a depressed melting point. The IR and $^1$H-NMR spectra of the product are identical to those of Compound (2) from Procedure C.

Compound (3)

4-(Diphenylamino)benzaldehyde N-(2,3-epoxypropyl)-N-phenylhydrazone (17 g, 40.5 mmole), ammonium thiocyanate (10 g, 0.13 mole, obtained from Aldrich), and 40 ml of tetrahydrofuran (THF) were added to a 100 ml, 3-neck round bottom flask equipped with a reflux condenser and a magnetic stirrer. The mixture was refluxed for 2 hours. The solvent was removed by evaporation and the residue was subjected to column chromatography (using silica gel, grade 62, 60-200 mesh, 150 Angstrom, obtained from Aldrich) using a mixture of acetone and hexane in a 1:4 ratio by volume as eluant. Fractions containing the product were collected, the solvent was evaporated, and the residue was recrystallized from benzene. The solid was filtered off and washed with isopropanol. The yield of the product, 4-(diphenylamino)benzaldehyde N-(2-thiiranylmethyl)-N-phenylhydrazone, was 12 g (68%). The $^1$H-NMR spectrum (100 MHz) of the product in CDCl$_3$ was characterized by the following chemical shifts (δ, ppm): 7.54 (s, 1H, CH=N); 7.50-6.90 (m, 19H, Ar); 5.06 (p, 1H, CH); 4.19 (d, 2H, NCH$_2$); and 3.72-3.32 (m, 2H, SCH$_2$). An elemental analysis yielded the following results in weight percent C 77.12, H 5.66, and N 9.49, which compared with calculated values for $C_{28}H_{25}N_3S$ in weight percent of C 77.21, H 5.79, and N 9.65.

Compound (3) may be prepared according to Procedure A for Compound (1) above except that 9-ethyl-3-carbazolecarboxaldehyde N-(2,3-epoxypropyl)-N-phenylhydrazone is replaced by 4-(diphenylamino)benzaldehyde N-(2-thiiranylmethyl)-N-phenylhydrazone. Alternatively, Compound (3) may be prepared according to Procedure B for Compound (1) above except that 9-ethyl-3-carbazolecarboxaldehyde N-(2,3-epoxypropyl)-N-phenylhydrazone is replaced by 4-(diphenylamino)benzaldehyde N-(2-thiiranylmethyl)-N-phenylhydrazone.

Compound (4)

4-Diethylamino-2-hydroxybenzaldehyde N,N-diphenylhydrazone. A solution of N,N-diphenylhydrazine hydrochloride (79.5 g, 0.36 mol, from Aldrich, Milwaukee, Wis.) in ethanol (500 ml) was slowly added to a solution of 4-diethylamino-2-hydroxybenzaldehyde (58.0 g, 0.3 mol, from Aldrich, Milwaukee, Wis.) in ethanol (500 ml) in the presence of excess sodium carbonate. The reaction mixture was refluxed until all of the aldehyde reacted in about ½ hour.

The residue obtained after evaporation of the solvent (800 ml) was treated with ether and the ether extract was washed with water until the pH of the water reached 7. The organic layer was dried over anhydrous magnesium sulphate, treated with activated charcoal, and filtered. The ether solvent was evaporated and the residue was recrystallized from ethanol. Crystalline 4-diethylamino-2-hydroxybenzaldehyde N,N-diphenylhydrazone was filtered off and washed with cold ethanol. The yield of the product was 85 g (78.8%). The melting point was found to be 95.5-96.5° C. (recrystallized from a mixture of 2-propanol and ether in a 10:1 ratio by volume). The $^1$H-NMR spectrum (100 MHz) of the product in $CDCl_3$ was characterized by the following chemical shifts (δ, ppm): 11.55 (s, 1H, OH); 7.55-6.95 (m, 11H, CH=N, Ph); 6.7 (d, J=8.6 Hz; 1H, 6-H of 1,2,4-subst. Ph); 6.23 (s, 1H, 3-H of 1,2,4-subst. Ph); 6.1 (d, J=8.6 Hz, 1H, 5-H of 1,2,4-subst. Ph); 3.3 (q, J=8.0 Hz, 4H, $CH_2$); 1.1 (t, J=8.0 Hz, 6H, $CH_3$). An elemental analysis yielded the following results in weight percent: C, 76.68; H, 7.75; N, 11.45, which compared with calculated values for $C_{23}H_{25}N_3O$ in weight percent of: C, 76.85; H, 7.01; N, 11.69.

4-Diethylamino-2-(2,3-epoxypropoxy)benzaldehyde N,N-diphenylhydrazone. A mixture of the 4-diethylamino-2-hydroxybenzaldehyde N,N-diphenylhydrazone (10.0 g, 27.82 mmol), 85% powdered potassium hydroxide (3.7 g, 0.05 mol), and anhydrous sodium sulfate (1.4 g, 11.13 mmol) in 35 ml of epichlorohydrin (commercially obtained from Aldrich, Milwaukee, Wis.) was stirred vigorously at 30-35° C. until the 4diethylamino-2-hydroxybenzaldehyde N,N-diphenylhydrazone disappeared (2.5 hours, as determined by thin layer chromatography (TLC)). After termination of the reaction by cooling the mixture to room temperature, the mixture was diluted with diethyl ether, and washed with copious amounts of water until the washed water reached a pH value of 7. The organic layer was dried over anhydrous magnesium sulfate, treated with activated charcoal, and filtered. The diethyl ether and unreacted epichlorohydrin were removed by evaporation under a vacuum. The crystals formed upon standing at room temperature were filtered off and washed with 2-propanol to yield 9.0 g (77.6%) of the product, 4-diethylamino-2-(2,3-epoxy-1-propoxy)benzaldehyde N,N-diphenylhydrazone. The melting point was found to be 86-87° C. (recrystallized from 10:1 v/v of 2-propanol:ether mixture). The $^1$H-NMR spectrum (100 MHz) of the product in $CDCl_3$ was characterized by the following chemical shifts (δ, ppm): 8.0 (d, 1H, 6-H of 1,2,4-subst. Ph); 7.8-7.0 (m, 1H, CH=N, Ph); 6.45 (d, 1H, 5-H of 1,2,4-subst. Ph); 6.1 (s, 1H, 3-H of 1,2,4-subst. Ph); 4.35-3.75 (m, 2H, $OCH_2$); 3.35 (q, 4H, $CH_2$); 3.05 (p, 1H, CH); 3.65 (t, 1H, one of $CH_2$ of oxirane); 2.45 (dd, 1H, one of $CH_2$ of oxirane); 1.15 (t, 6H, $CH_3$). Elemental analysis yielded the following values in weight percent: C, 74.95; H, 6.88; N, 9.92, which compared with calculated values for $C_{26}H_{29}N_3O_2$ in weight percent of: C, 75.15; H, 7.03; N, 10.11.

Compound (4) may be prepared according to Procedure A for Compound (1) above except that 9-ethyl-3-carbazolecarboxaldehyde N-(2,3-epoxypropyl)-N-phenylhydrazone is replaced by 4-diethylamino-2-(2,3-epoxypropoxy)benzaldehyde N,N-diphenylhydrazone. Alternatively, Compound (4) may be prepared according to Procedure B for Compound (1) above except that 9-ethyl-3-carbazolecarboxaldehyde N-(2,3-epoxypropyl)-N-phenylhydrazone is replaced by 4-diethylamino-2-(2,3-epoxypropoxy)benzaldehyde N,N-diphenylhydrazone.

Compound (5)

9-Ethyl-3-carbazolecarboxaldehyde hydrazone. A quantity of 98% hydrazine monohydrate (50 ml, 1.4 mole, obtained from Aldrich, Milwaukee, Wis.) and 10 ml of triethylamine (obtained from Aldrich, Milwaukee, Wis.) were added to a 250 ml, 2-neck round bottom flask equipped with a mechanical stirrer and an addition funnel. The solution was stirred vigorously at room temperature for a period of 10-15 min. A solution of 9-ethyl-3-carbazolecarboxaldehyde (22.3 g, 0.1 mol, from Aldrich, Milwaukee, Wis.) in 30 ml of tetrahydrofuran (THF) was added slowly to the round bottom flask. After the addition of aldehyde was completed, the reaction mixture was stirred at room temperature for 2 hours. Then, the reaction mixture was diluted with 50 ml of water. A precipitate was collected by filtration and washed repeatedly with water to give crude, i.e. without further purification, 9-ethyl-3-carbazolecarboxaldehyde hydrazone, which was used immediately in the next step.

9-Ethyl-3-carbazolecarboxaldehyde 2-hydroxy-1-naphthaldehyde azine. The crude 9-ethyl-3-carbazolecarboxaldehyde hydrazone (23.7 g, 0.1 mole, obtained in the previous step) were added to a refluxed solution of 2-hydroxy-1-naphthaldehyde (17.2 g, 0.1 mol, obtained from Aldrich, Milwaukee, Wis.) in 50 ml of dioxane. The reflux process was continued for 10-15 min, and then the reaction mixture was allowed to stand at room temperature. The crystals formed upon standing were filtered off and washed with 2-propanol and ether to yield 38 g (97%) of the product, 9-ethyl-3-carbazolecarboxaldehyde 2-hydroxy-1-naphthaldehyde azine. The product was recrystallized from dioxane to give a solid with a melting point of 184-186° C. (from dioxane). The $^1$H-NMR spectrum (100 MHz) of the product in $CDCl_3$ was characterized by the following chemical shifts (δ, ppm): 13.5 (s, 1H, OH); 9.7 (s, 1H, one of CH=N); 8.8 (s, 1H, one of CH=N); 8.5 (s, 1H, 4-H Ht); 8.3-7.1 (m, 12H, Ar); 4.3 (q, J=7.1 Hz, 2H, $NCH_2CH_3$); 1.4 (t, 3H, J=7.1 Hz, $NCH_2CH_3$). An elemental analysis yielded in weight %: C=79.59; H=5.38; N=10.52, which compared to calculated values for $C_{26}H_{21}N_3O$ of (weight %): C=79.77; H=5.41; N=10.73.

9-Ethyl-3-carbazolecarboxaldehyde 2-(2,3-epoxypropoxy)-1-naphthaldehyde azine. A mixture of 9-ethyl-3-carbazolecarboxaldehyde 2-hydroxy-1-naphthaldehyde azine (27.4 g, 0.07 mol, prepared in previous step) and epichlorohydrin (80 ml, 1 mol, obtained from Aldrich, Milwaukee, Wis.) was added to a 250 ml 3-neck round bottom flask equipped with a reflux condenser, a thermometer and a mechanical stirrer. The reaction mixture was stirred vigorously at 35-40° C. for 24 h. Six periodically delivered portions of powdered 85% potassium hydroxide (26.8 g, 0.4 mol) and anhydrous sodium sulphate (6.8 g, 0.05 mol), were added during the reaction time, temporarily cooling the reaction mixture to 20-25° C. prior to each addition. After terminating the reaction, the mixture was cooled to room temperature and filtered. The organic phase was treated with ethyl acetate and washed with distilled water until the wash water was neutral. The organic layer was dried over anhydrous magnesium sulfate, treated with activated charcoal, and filtered. The solvent was removed by evaporation and the residue was subjected to column chromatography (silica gel, grade 62, 60-200 mesh, 150 Å, Aldrich, Milwaukee, Wis.) using 1:4 by volume acetone: hexane as the eluant. Fractions containing the product were collected and the solvent evaporated to afford an oily residue that was dissolved in the 30 ml of methanol/toluene at a 1/1 volume ratio. The crystals formed upon standing were filtered off and washed with 2-propanol to give 18 g (for a 57% yield)

of compound (2). The product, 9-ethyl-3-carbazolecarboxaldehyde 2-(2,3-epoxypropoxy)-1-naphthaldehyde azine, had a melting point of 164.5-165.5° C. (from methanol/toluene, 1/1 volume ratio). The $^1$H-NMR spectrum (100 MHz) of the product in $CDCl_3$ was characterized by the following chemical shifts (δ, ppm): 9.5 (m, 1H, one of CH=N); 9.0 (s, 1H, one of CH=N); 8.6 (s, 1H, 4-HHt); 8.3-7.2 (m, 12H, Ar); 4.6-4.0 (m, 4H, $OCH_2$, $NC\underline{H}_2CH_3$); 3.45 (m, 1H, CH); 2.9 (dd, 1H, one of $CH_2$ of oxirane); 2.7 (dd, 1H, one of $CH_2$ of oxirane); 1.4 (t, 3H, $CH_3$). An elemental analysis yielded in weight %: C=77.62; H=5.31; N=9.17, which compared with calculated values for $C_{29}H_{25}N_3O_2$ in weight % of: C=77.83; H=5.63; N=9.39.

Compound (5) may be prepared according to Procedure A for Compound (1) above except that 9-ethyl-3-carbazolecarboxaldehyde N-(2,3-epoxypropyl)-N-phenylhydrazone is replaced by 9-ethyl-3-carbazolecarboxaldehyde 2-(2,3-epoxypropoxy)-1-naphthaldehyde azine. Alternatively, Compound (5) may be prepared according to Procedure B for Compound (1) above except that 9-ethyl-3-carbazolecarboxaldehyde N-(2,3-epoxypropyl)-N-phenylhydrazone is replaced by 9-ethyl-3-carbazolecarboxaldehyde 2-(2,3-epoxypropoxy)-1-naphthaldehyde azine.

Compound (6)

10-Ethylphenothiazine. A mixture of 10 g (0.05 mol) of phenothiazine (obtained from Fluka), 11.7 g (0.075 mol) of iodoethane (obtained from Aldrich), 4.2 g (0.075 mol) of potassium hydroxide, and 0.25 g of tetra-n-butylammonium hydrogen sulfate (obtained from Aldrich) in 200 ml of dry toluene was refluxed for 24 hours. After cooling, the reaction mixture was filtered, and the solvent was evaporated. The product was crystallized from methanol. The yield of 10-ethylphenothiazine was 10.2 g (90%). The melting point of the product was 103-104° C. The $^1$H-NMR spectrum (100 MHz) of the product in $CDCl_3$ was characterized by the following chemical shifts (δ, ppm): 1.40 (t, J=7.0 Hz, 3H, $CH_3$); 3.90 (q, J=7.0 Hz, 2H, $CH_2$); 6.78-7.32 (m, 8H, Ar).

10-Ethylphenothiazine-3-carbaldehyde. Phosphorus oxychloride ($POCl_3$, 3.7 ml, 0.04 mol, obtained from Aldrich) was added dropwise to 4.4 ml (0.06 mol) of dry dimethylformamide (DMF) at 0° C. under a nitrogen atmosphere. This solution was warmed up slowly to room temperature. Next, a solution of 5 g (0.02 mol) of 10-ethylphenothiazine in 5 ml dry DMF was added dropwise. The reaction mixture was refluxed at 80° C. for 24 hours and poured into ice water. This solution was neutralized with potassium hydroxide until the pH reached 6-8. The product was extracted with chloroform. The chloroform extract was dried with anhydrous sodium sulfate, filtered, and distilled. The product was recrystallized from methanol. The yield of 10-ethylphenothiazine-3-carbaldehyde was 3.7 g (66%). The melting point of the product was 94-95° C. (crystallized from methanol). The $^1$H-NMR spectrum (100 MHz) of the product in $CDCl_3$ was characterized by the following chemical shifts (δ, ppm): 1.50 (t, J=7.0 Hz, 3H, $CH_3$); 4.02 (q, J=7.0 Hz, 2H, $CH_2$); 6.95-6.39 (m, 5H, Ar), 7.52-7.70 (m, 2H, Ar), 9.83 (s, 1H, CHO).

10-Ethylphenothiazine-3-carbaldehyde N-phenylhydrazone. 10-Ethylphenothiazine-3-carbaldehyde (3 g, 0.012 mol) was dissolved in 30 ml of methanol under mild heating. A solution of 1.9 g (0.018 mol) of N-phenylhydrazine (obtained from Aldrich) in methanol was added to the cooled reaction mixture. Next, the reaction mixture was refluxed for 0.5 hour. The precipitated product was filtered, washed with a large amount of methanol, and dried. The yield of yellowish crystals of 10-ethylphenothiazine-3-carbaldehyde N-phenylhydrazone was 3 g (75%).

10-Ethylphenothiazine-3-carbaldehyde N-(2,3-epoxypropyl)-N-phenylhydrazone. 10-Ethylphenothiazine-3-carbaldehyde N-phenylhydrazone (2 g, 0.0058 mol) was dissolved in epichlorohydrin (4 g, 0.043 mol, obtained from Aldrich,). A 0.9 g (0.017 mol) quantity of KOH was added to the reaction mixture in three portions. Anhydrous sodium sulfate (0.33 g, 0.0023 mol) was also added during the first addition of KOH. The reaction mixture was stirred at 30° C. for 24 hours and then the crude product was extracted with diethyl ether. The solvent and epichlorohydrin were removed by vacuum evaporation. The crude product was purified by column chromatography with silica gel (grade 62, 60-200 mesh, 150 Å, Aldrich) and an eluant mixture of ethyl acetate and n-hexane in a volume ratio of 1:3. The yield of 10-ethylphenothiazine-3-carbaldehyde N-(2,3-epoxypropyl) N-phenylhydrazone was 1.4 g (60%). The $^1$H-NMR spectrum (100 MHz) of the product in $CDCl_3$ was characterized by the following chemical shifts (δ, ppm): 1.33 (t, 3H, $CH_3$); 2.52-2.68 (dd, 1H, one of $CH_2O$); 2.72-2.95 (dd, 1H, one of $CH_2O$); 3.63-4.12 (m, 3H, $CH,CH_3C\underline{H}_2N$); 4.21 (d, 2H, $CH_2N$)); 6.55-7.92 (m, 12H, Ar); .8.05 (s, CH=N).

Compound (6) may be prepared according to Procedure A for Compound (1) above except that 9-ethyl-3-carbazolecarboxaldehyde N-(2,3-epoxypropyl)-N-phenylhydrazone is replaced by 10-ethylphenothiazine-3-carbaldehyde N-(2, 3-epoxypropyl) N-phenylhydrazone. Alternatively, Compound (6) may be prepared according to Procedure B for Compound (1) above except that 9-ethyl-3-carbazolecarboxaldehyde N-(2,3-epoxypropyl)-N-phenylhydrazone is replaced by 10-ethylphenothiazine-3-carbaldehyde N-(2,3-epoxypropyl) N-phenylhydrazone.

Compound (7)

1,3-Bis(4,4'-dimethyldiphenylamino)-4-methoxybenzene. A mixture of 9.7 g (0.07 mol) of 4-methoxy-1,3-phenylenediamine (obtained from 4-methoxy-1,3-phenylenediamine sulfate hydrate, Aldrich), 76.3 g (0.35 mol) of 4-iodotoluene, 48.3 g (0.35 mol) of powdered anhydrous potassium carbonate, 4.44 g (0.07 mol) of electrolytic copper powder (obtained from Aldrich), and 2 g (3.78 mmol) of 18-crown-6 (obtained from Aldrich) were refluxed in 50 ml of o-dichlorobenzene under argon for 24 hours. The copper and inorganic salts were then removed by filtration of the hot reaction mixture. The solvent was distilled under reduced pressure and a crude 1,3-bis(4,4'-dimethyldiphenylamino)-4-methoxybenzene product was purified by column chromatography with silica gel (grade 62, 60-200 mesh, 150 Å, Aldrich) using a mixture of n-hexane:1,2-dichloroethane in a volume ratio of 5:1 as eluant. The yield of 1,3-bis(4,4'-dimethyldiphenylamino)-4-methoxybenzene was 23.2 g (66%). The product had a melting point of 168.5-170° C. (recrystallized from n-hexane). The $^1$H-NMR spectrum (100 MHz) of the product in $CDCl_3$ was characterized by the following chemical shifts (δ, ppm): 7.0-6.6 (m, 19H, Ar); 3.55 (s, 3H, $OCH_3$); 2.2 (s, 12H, $CH_3$). An infrared spectrum yielded the following peaks ($cm^{-1}$): 3030 ($CH_{arom}$); 2945, 2910, 2860, 2835 ($CH_{aliph}$); 1120, 1105 (C—O—C). An elemental analysis yielded the following values in weight %: C, 84.25; H, 6.80; N, 5.64, which compare to calculated values for $C_{35}H_{34}N_2O$ in weight % of: C, 84.30; H, 6.87; N, 5.62.

1,3-Bis(4,4'-dimethyldiphenylamino)-4-hydroxybenzene. A quantity of 1,3-bis(4,4'-dimethyldiphenylamino)-4-methoxybenzene (20 g, 0.04 mol) was dissolved in 100 ml of methylene chloride at 0° C. To the resulting solution, 100 ml of a solution of boron tribromide (1.0 M, obtained from Aldrich) was added. The mixture was stirred at 0° C. for 24 hours. Then, the mixture was washed thoroughly with distilled water. The crude product 1,3-bis(4,4'-dimethyldiphenylamino)-4-hydroxybenzene was obtained by evaporating methylene chloride. The crude product was purified by column chromatography with silica gel (grade 62, 60-200 mesh, 150 Å, Aldrich) using a mixture of n-hexane:1,2-dichloroethane in a volume ratio of 4:1 as eluant. The yield of 1,3-bis(4,4'-dimethyldiphenylamino)-4-hydroxybenzene was 15 g (77%). The structure was confirmed by electron-impact mass spectroscopy (MS-EI): 484 ($M^+$).

1,3-Bis(4,4'-dimethyldiphenylamino)-4-(2,3-epoxypropoxy)benzene. A 6.8 g (14 mmol) quantity of 1,3-bis(4,4'-dimethyldiphenylamino)-4-hydroxybenzene and 32 ml (0.4 mol) of epichlorohydrin (commercially obtained from Aldrich, Milwaukee, Wis.) were added to a 50 ml 3-neck round bottom flask equipped with reflux condenser, thermometer and mechanical stirrer to form a reaction mixture. The reaction mixture was stirred vigorously at 35-40° C. for 7 hours. While the reaction mixture was stirring, 2.7 g (0.04 mol) of powdered 85% potassium hydroxide and 0.7 g (5 mmol) of anhydrous sodium sulfate were added in two portions, with a temporary cooling of the reaction mixture to 20-25 C prior to each addition. After termination of the reaction, the mixture was cooled to room temperature and filtered. The organic part of the mixture was treated with diethylether and washed with distilled water until the wash water had a neutral pH. After the organic solution was dried over anhydrous magnesium sulfate, it was treated with activated charcoal, filtered, and the solvent was removed by evaporation. The residue was purified by column chromatography (silica gel, grade 62, 60-200 mesh, 150 Å, Aldrich) using a mixture of acetone:hexane in a volume ratio of 1:4 as the eluant. Fractions containing the product were collected and the solvent was evaporated to yield 4.8 g (63%) of 1,3-bis(4,4'-dimethyldiphenylamino)-4-(2,3-epoxypropoxy)benzene. The $^1$H-NMR spectrum (250 MHz) of the product in $CDCl_3$ was characterized by the following chemical shifts (δ, ppm): 7.05-6.70 (m, 19H, Ar); 3.84 (d, J=4.0 Hz, $OCH_2$); 2.84 (m, 1H, CH); 2.33 (dd, 1H, one of $CH_2$ of oxirane); and 2.27 (s, 12H, $CH_3$). An elemental analysis resulted in the following values in weight %: C, 82.08; H, 6.61; N, 5.07, which compared with calculated values for $C_{37}H_{36}N_2O_2$ in weight percent of: C, 82.19; H, 6.71; N 5.18.

Compound (7) may be prepared according to Procedure A for Compound (1) above except that 9-ethyl-3-carbazolecarboxaldehyde N-(2,3-epoxypropyl)-N-phenylhydrazone is replaced by 1,3-bis(4,4'-dimethyldiphenylamino)-4-(2,3-epoxypropoxy)benzene. Alternatively, Compound (7) may be prepared according to Procedure B for Compound (1) above except that 9-ethyl-3-carbazolecarboxaldehyde N-(2,3-epoxypropyl)-N-phenylhydrazone is replaced by 1,3-bis(4,4'-dimethyldiphenylamino)-4-(2,3-epoxypropoxy)benzene.

Compound (8)

9-(2,3-Epoxypropyl)carbazole. 9-(2,3-Epoxypropyl)carbazole may be prepared by the reaction between carbazole and epichlorohydrin in the presence of a base. Alternatively, 9-(2,3-epoxypropyl)carbazole may be obtained from Biolar, Rupnicu str. 3, Olaine LV-2114, Latvia; Phone: +371 7964101, Fax: +371 7966555.

9-(2-Hydroxy-3-chloropropyl)carbazole. 9-(2-hydroxy-3-chloropropyl)carbazole may be prepared by the ring opening reaction of the oxirane ring of 9-(2,3-epoxypropyl)carbazole with hydrochloric acid according to a procedure similar to that described by A. Stanisauskaite et el. in "Synthesis of epoxypropylderivatives of hydrazones", Chemija, 1996,3, 68-73.

9-(2-Acetyloxy-3-chloropropyl)carbazole. 9-(2-Acetyloxy-3-chloropropyl)carbazole may be prepared by the esterification reaction of 9-(2-hydroxy-3-chloropropyl)carbazole with acetic anhydride or acetyl halide.

9-(2,3-Epoxypropyl)-3-Carbazolecarboxaldehyde N,N-Diphenylhydrazone. 9-(2-Acetyloxy-3-chloropropyl)carbazolecarboxaldehyde may be prepared by the Vilsmeier reaction between 9-(2-acetyloxy-3-chloropropyl)carbazole and a mixture of phosphorus oxychloride and N,N-dimethylformamide. 9-(2-Acetyloxy-3-chloropropyl)carbazolecarboxaldehyde N,N-diphenylhydrazone may be prepared by the reaction between 9-(2-acetyloxy-3-chloropropyl)carbazolecarboxaldehyde and N,N-diphenylhydrazine. 9-(2,3-Epoxypropyl)-3-carbazolecarboxaldehyde N,N-diphenylhydrazone may be prepared by refluxing 9-(2-acetyloxy-3-chloropropyl)carbazole-3-carboxaldehyde N,N-diphenylhydrazone in acetone in the presence of a base (such as potassium hydroxide and sodium hydroxide).

Compound (8) may be prepared according to Procedure A for Compound (1) above except that 9-ethyl-3-carbazolecarboxaldehyde N-(2,3-epoxypropyl)-N-phenylhydrazone is replaced by 9-(2,3-epoxypropyl)-3-carbazolecarboxaldehyde N,N-diphenylhydrazone. Alternatively, Compound (8) may be prepared according to Procedure B for Compound (1) above except that 9-ethyl-3-carbazolecarboxaldehyde N-(2,3-epoxypropyl)-N-phenylhydrazone is replaced by 9-(2,3-epoxypropyl)-3-carbazolecarboxaldehyde N,N-diphenylhydrazone.

Compound (9)

9-(2-Acetyloxy-3-chloropropyl)carbazole-3,6-dicarboxaldehyde. 9-(2-Acetyloxy-3-chloropropyl)carbazole-3,6-dicarboxaldehyde may be prepared by the Vilsmeier reaction between 9-(2-acetyloxy-3-chloropropyl)carbazole (disclosed previously) and a mixture of phosphorus oxychloride and N,N-dimethylformamide.

9-(2,3-Epoxypropyl)carbazole-3,6-dicarboxaldehyde Bis (N,N-Diphenylhydrazone). 9-(2-Acetyloxy-3-chloropropyl)carbazole-3,6-dicarboxaldehyde bis(N,N-diphenylhydrazone) may be prepared by the reaction between 9-(2-acetyloxy-3chloropropyl)carbazole-3,6-dicarboxaldehyde and N,N-diphenylhydrazine. 9-(2,3-Epoxypropyl)carbazole-3,6-dicarboxaldehyde bis(N,N-diphenylhydrazone) may be prepared by refluxing 9-(2-acetyloxy-3-chloropropyl)carbazole-3,6-dicarboxaldehyde bis(N,N-diphenylhydrazone) in acetone in the presence of a base (such as potassium hydroxide and sodium hydroxide).

Compound (9) may be prepared according to Procedure A for Compound (1) above except that 9-ethyl-3-carbazolecarboxaldehyde N-(2,3-epoxypropyl)-N-phenylhydrazone is replaced by 9-(2,3-epoxypropyl)-carbazole-3,6-dicarboxaldehyde bis(N,N-diphenylhydrazone). Alternatively, Compound (9) may be prepared according to Procedure B for Compound (1) above except that 9-ethyl-3-carbazolecarboxaldehyde N-(2,3-epoxypropyl)-N-phenylhydrazone is replaced by 9-(2,3-epoxypropyl)-carbazole-3,6-dicarboxaldehyde bis(N,N-diphenylhydrazone).

Compound (10)

9-(2-acetyloxy-3-chloropropyl)-3,6-bis(2,2-diphenylvinyl)carbazole. The compound 9-(2-acetyloxy-3-chloropropyl)-3,6-bis(2,2-diphenylvinyl)carbazole may be prepared by the reaction between 9-(2-acetyloxy-3-chloropropyl)carbazole-3,6-dicarboxaldehyde (disclosed previously) and diethyl benzhydryl phosphonate (from Midori Kagaku Co., Ltd, Tokyo, Japan) in the presence of a strong base, such as sodium hydride, n-butyllithium, potassium-t-butoxide, or lithium ethoxide. Such reactions between phosphonate carbanions and carbonyl compounds are described in Carey et al., "Advanced Organic Chemistry, Part B: Reactions and Synthesis," New York, 1983, pp. 74-78, which is incorporated herein by reference. Specifically, diethyl benzhydryl phosphonate and 9-(2-acetyloxy-3-chloropropyl)-carbazole-3,6-dicarboxaldehyde in a molar ration of 2:1 are dissolved in DMF, followed by adding a strong base, such as potassium-t-butoxide, under cooling with stirring. The reaction mixture is stirred at room temperature until the reaction is complete. The product 9-(2-acetyloxy-3-chloropropyl)-3,6-bis(2,2-diphenylvinyl)carbazole is isolated and purified.

9-(2,3-Epoxypropyl)-3,6-Bis(2,2-diphenylvinyl)Carbazole. 9-(2,3-Epoxypropyl)-3,6-bis(2,2-diphenylvinyl)carbazole may be prepared by refluxing 9-(2acetyloxy-3-chloropropyl)-3,6-bis(2,2-diphenylvinyl)carbazole in acetone in the presence of a base (such as potassium hydroxide and sodium hydroxide).

Compound (10) may be prepared according to Procedure A for Compound (1) above except that 9-ethyl-3-carbazolecarboxaldehyde N-(2,3-epoxypropyl)-N-phenylhydrazone is replaced by 9-(2,3-epoxypropyl)-3,6-bis(2,2-diphenylvinyl)-carbazole. Alternatively, Compound (10) may be prepared according to Procedure B for Compound (1) above except that 9-ethyl-3-carbazolecarboxaldehyde N-(2,3-epoxypropyl)-N-phenylhydrazone is replaced by 9-(2,3-epoxypropyl)-3,6-bis(2,2-diphenylvinyl)-carbazole.

Example 2

Charge Mobility Measurements

This example describes the measurement of charge mobility and ionization potential for charge transport materials, specifically Compound (1) by Procedures A and B and Compound (2) by Procedures C and D.

Sample 1

A mixture of 0.1 g of the Compound (1) prepared by Procedure A and 0.1 g of polyvinylbutyral (S-LEC B BX-1, commercially obtained from Sekisui) was dissolved in 2 ml of tetrahydrofuran (THF). The solution was coated on a polyester film with a conductive aluminum layer by a dip roller. After the coating was dried for 1 hour at 80° C., a clear 10 μm thick layer was formed. The hole mobility of the sample was measured and the results are presented in Table 1.

Sample 2

Sample 2 was prepared and tested similarly as Sample 1, except Compound (1) prepared by Procedure A was replaced by Compound (1) prepared by Procedure B.

Sample 3

Sample 3 was prepared and tested similarly as Sample 1, except Compound (1) prepared by Procedure A was replaced by Compound (2) prepared by Procedure C.

Sample 4

Sample 4 was prepared and tested similarly as Sample 3, except Compound (2) prepared by Procedure C was replaced by Compound (2) Procedure D.

Mobility Measurements

Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747-752, incorporated herein by reference. The hole mobility measurement was repeated with appropriate changes to the charging regime to charge the sample to different U values, which corresponded to different electric field strength inside the layer E. This dependence on electric field strength was approximated by the formula $$\mu = \mu_0 e^{\alpha \sqrt{E}}$$

Here E is electric field strength, $\mu_0$ is the zero field mobility and $\alpha$ is Pool-Frenkel parameter. Table 1 lists the mobility characterizing parameters $\mu_0$ and $\alpha$ values and the mobility value at the $6.4 \times 10^5$ V/cm field strength as determined by these measurements for the four samples.

TABLE 1

| Example | $\mu_0$ (cm$^2$/V · s) | $\mu$ (cm$^2$/V · s) at 6.4 · 10$^5$ V/cm | $\alpha$ (cm/V)$^{0.5}$ | Ionization Potential (eV) |
|---|---|---|---|---|
| Compound (1) by Procedure A | / | / | / | 5.27 |
| Compound (1) by Procedure B | / | / | / | 5.25 |
| Compound (2) by Procedure C | / | / | / | 5.38 |
| Compound (2) by Procedure D | / | / | / | 5.39 |
| Sample 1 | $1.7 \times 10^{-9}$ | $4.0 \times 10^{-7}$ | 0.0069 | / |
| Sample 2 | $1.5 \times 10^{-9}$ | $3.3 \times 10^{-7}$ | 0.0068 | / |
| Sample 3 | $2.8 \times 10^{-8}$ | $1.8 \times 10^{-6}$ | 0.0052 | / |
| Sample 4 | $2.4 \times 10^{-8}$ | $1.9 \times 10^{-6}$ | 0.0054 | / |

Example 3

Ionization Potential Measurements

This example describes the measurement of the ionization potential for the charge transport materials described in Example 1.

To perform the ionization potential measurements, a thin layer of a charge transport material about 0.5 μm thickness was coated from a solution of 2 mg of the charge transport material in 0.2 ml of tetrahydrofuran on a 20 cm$^2$ substrate surface. The substrate was an aluminized polyester film coated with a 0.4 μm thick methylcellulose sub-layer.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127-131, incorporated herein by reference. In particular, each sample was illuminated with monochromatic light from the quartz monochromator with a deuterium lamp source. The power of the incident light beam was 2-5·10$^{-8}$ W. A negative voltage of −300 V was supplied to the sample substrate. A counter-electrode with the 4.5×15 mm$^2$ slit for illumination was placed at 8 mm distance from the sample surface. The counter-electrode was connected to the input of a BK2-16 type electrometer, working in the open input regime, for the photocurrent measurement. A $10^{-15}$-$10^{-12}$ amp photocurrent was flowing in the circuit under illumination. The photocurrent, I, was strongly dependent on the incident light photon energy hν.

The $I^{0.5}$=f(hv) dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography*, 28, Nr. 4, p. 364 (1989) by E. Miyamoto, Y. Yamaguchi, and M. Yokoyama; and "Photoemission in Solids," Topics in Applied Physics, 26, 1-103 (1978) by M. Cordona and L. Ley, both of which are incorporated herein by reference). The linear part of this dependence was extrapolated to the hv axis, and the Ip value was determined as the photon energy at the interception point. The ionization potential measurement has an error of ±0.03 eV. The ionization potential values are given in Table 1 above.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:
   (a) a charge transport material having the formula

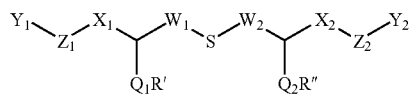

where $Z_1$ and $Z_2$ comprise, each independently, a bond, a vinyl group, or a —$CR_3$=N—N=$CR_4$— group;
   $Y_1$ and $Y_2$ comprise, each independently, an aromatic group;
   $X_1$ and $X_2$ are, each independently, a linking group;
   $W_1$ and $W_2$ are, each independently, a —$(CH_2)_n$— group or a —$(CH_2)_{n-1}$—C(=O)— group, where n is an integer between 1 and 10, inclusive;
   $Q_1$ and $Q_2$ are, each independently, O, S, or NR; and
   $R_1$, $R_2$, $R_3$, $R_4$, R, R', and R" comprise, each independently, H, an alkyl group, an alkenyl group, an alkynyl group, an acyl group, a heterocyclic group, or an aromatic group; and
   (b) a charge generating compound.

2. An organophotoreceptor according to claim 1 wherein $Y_1$ and $Y_2$ comprise, each independently, an aryl group selected from the group consisting of a phenyl group, a naphthyl group, a bis[(N,N-disubstituted)amino]aryl group, a julolidinyl group, an (N-substituted)arylamine group, and an (N,N-disubstituted)arylamine group.

3. An organophotoreceptor according to claim 1 wherein $Y_1$ and $Y_2$ comprise, each independently, an aromatic heterocyclic group selected from the group consisting of a furanyl group, a thiophenyl group, a pyrrolyl group, an indolyl group, a carbazolyl group, a benzofuranyl group, a benzothiophenyl group, a dibenzofuranyl group, a dibenzothiophenyl group, a pyridinyl group, a pyridazinyl group, a pyrimidinyl group, a pyrazinyl group, a triazinyl group, a tetrazinyl group, a petazinyl group, a quinolinyl group, an isoquinolinyl group, a cinnolinyl group, a phthalazinyl group, a quinazolinyl group, a quinoxalinyl group, a naphthyridinyl group, an acridinyl group, a phenanthridinyl group, a phenanthrolinyl group, an anthyridinyl group, a purinyl group, a pteridinyl group, an alloxazinyl group, a phenazinyl group, a phenothiazinyl group, a phenoxazinyl group, a phenoxathiinyl group, a dibenzo(1,4)dioxinyl group, a thianthrenyl group, a bicarbazolyl group, and a 1,6-di(10H-10-phenothiazinyl)hexyl group.

4. An organophotoreceptor according to claim 2 wherein the aryl group further comprises at least a substituent selected from the group consisting of an alkyl group, an alkenyl group, an alkynyl group, an acyl group, an aromatic group, a heterocyclic group, an amino group, an (N,N-disubstituted)hydrazone group, an enamine group, an azine group, an epoxy group, a thiiranyl group, and an aziridinyl group.

5. An organophotoreceptor according to claim 1 wherein $X_1$ and $X_2$ are, each independently, a —$(CH_2)_m$— group, where m is an integer between 1 and 20, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkenyl group, an alkynyl group, an acyl group, a heterocyclic group, an aromatic group, or a part of a ring group.

6. An organophotoreceptor according to claim 5 wherein $X_1$ and $X_2$ are, each independently, a —$CH_2$— group, a —$OCH_2$— group, or a —Ar—$OCH_2$— group; $Y_1$ and $Y_2$ comprise, each independently, an aryl group or an aromatic heterocyclic group; and W and $W_2$ are, each independently, a bond, a —$CH_2$— group, a —$CH_2CH_2$— group, or a —$(CH_2)_{n-1}$—C(=O)— group, where n is an integer between 2 and 6 and Ar comprises an aromatic group.

7. An organophotoreceptor according to claim 6 wherein the aryl group or the aromatic heterocyclic group is selected from the group consisting of the following formulae:

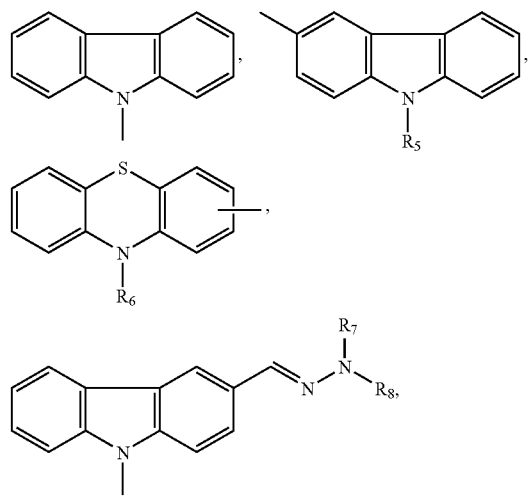

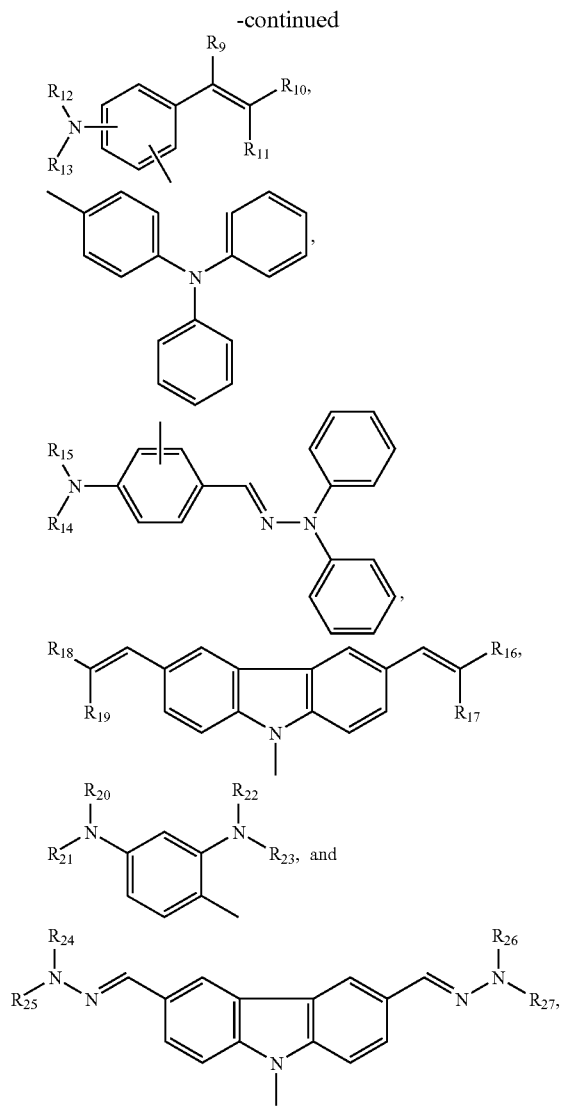

where $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ comprise, each independently, H, an alkyl group, an alkenyl group, an alkynyl group, an acyl group, an aromatic group, or a heterocyclic group.

8. An organophotoreceptor according to claim 7 wherein the aryl group or the aromatic heterocyclic group further comprises at least a substituent selected from the group consisting of an alkyl group, an alkenyl group, an alkynyl group, an acyl group, an aromatic group, a heterocyclic group, an (N,N-disubstituted)hydrazone group, an enamine group, and an azine group.

9. An organophotoreceptor according to claim 1 wherein the photoconductive element further comprises a second charge transport material.

10. An organophotoreceptor according to claim 9 wherein the second charge transport material comprises an electron transport compound.

11. An organophotoreceptor according to claim 1 wherein the photoconductive element further comprises a binder.

12. An electrophotographic imaging apparatus comprising:
(a) a light imaging component; and
(b) an organophotoreceptor oriented to receive light from the light imaging component, the organophotoreceptor comprising an electrically conductive substrate and a photoconductive element on the electrically conductive substrate, the photoconductive element comprising:
(i) a charge transport material having the formula

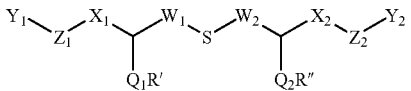

where $Z_1$ and $Z_2$ comprise, each independently, a bond, a vinyl group, or a —$CR_3$=N—N=$CR_4$— group;
$Y_1$ and $Y_2$ comprise, each independently, an aromatic group;
$X_1$ and $X_2$ are, each independently, a linking group;
$W_1$ and $W_2$ are, each independently, a —$(CH_2)_n$— group or a —$(CH_2)_{n-1}$—C(=O)— group, where n is an integer between 1 and 10, inclusive;
$Q_1$ and $Q_2$ are, each independently, O, S, or NR; and
$R_1$, $R_2$, $R_3$, $R_4$, R, R', and R" comprise, each independently, H, an alkyl group, an alkenyl group, an alkynyl group, an acyl group, a heterocyclic group, or an aromatic group; and
(ii) a charge generating compound.

13. An electrophotographic imaging apparatus according to claim 12 wherein $Y_1$ and $Y_2$ comprise, each independently, an aryl group selected from the group consisting of a phenyl group, a naphthyl group, a bis[(N,N-disubstituted)amino]aryl group, a julolidinyl group, an (N-substituted) arylamine group, and an (N,N-disubstituted)arylamine group.

14. An electrophotographic imaging apparatus according to claim 12 wherein $Y_1$ and $Y_2$ comprise, each independently, an aromatic heterocyclic group selected from the group consisting of a furanyl group, a thiophenyl group, a pyrrolyl group, an indolyl group, a carbazolyl group, a benzofuranyl group, a benzothiophenyl group, a dibenzofuranyl group, a dibenzothiophenyl group, a pyridinyl group, a pyridazinyl group, a pyrimidinyl group, a pyrazinyl group, a triazinyl group, a tetrazinyl group, a petazinyl group, a quinolinyl group, an isoquinolinyl group, a cinnolinyl group, a phthalazinyl group, a quinazolinyl group, a quinoxalinyl group, a naphthyridinyl group, an acridinyl group, a phenanthridinyl group, a phenanthrolinyl group, an anthyridinyl group, a purinyl group, a pteridinyl group, an alloxazinyl group, a phenazinyl group, a phenothiazinyl group, a phenoxazinyl group, a phenoxathiinyl group, a dibenzo(1,4)dioxinyl group, a thianthrenyl group, a bicarbazolyl group, and a 1,6-di(10H-10-phenothiazinyl)hexyl group.

15. An electrophotographic imaging apparatus according to claim 13 wherein the aryl group further comprises at least a substituent selected from the group consisting of an alkyl group, an alkenyl group, an alkynyl group, an acyl group, an aromatic group, a heterocyclic group, an amino group, an (N,N-disubstituted)hydrazone group, an enamine group, an azine group, an epoxy group, a thiiranyl group, and an aziridinyl group.

16. An electrophotographic imaging apparatus according to claim 12 wherein $X_1$ and $X_2$ are, each independently, a —$(CH_2)_m$— group, where m is an integer between 1 and 20, inclusive, and one or more of the methylene groups is optionally replaced by O, S, N, C, B, Si, P, C=O, O=S=O, a heterocyclic group, an aromatic group, an $NR_a$ group, a CR$_b$ group, a CR$_c$R$_d$ group, or a SiR$_e$R$_f$ where R$_a$, R$_b$, R$_c$, R$_d$, R$_e$, and R$_f$ are, each independently, a bond, H, a hydroxyl group, a thiol group, a carboxyl group, an amino group, an alkyl group, an alkoxy group, an alkylsulfanyl group, an alkenyl group, an alkynyl group, an acyl group, a heterocyclic group, an aromatic group, or a part of a ring group.

17. An electrophotographic imaging apparatus according to claim 16 wherein X$_1$ and X$_2$ are, each independently, a —CH$_2$— group, a —OCH$_2$— group, or a —Ar—OCH$_2$— group; Y$_1$ and Y$_2$ comprise, each independently, an aryl group or an aromatic heterocyclic group; and W$_1$ and W$_2$ are, each independently, a bond, a —CH$_2$— group, a —CH$_2$CH$_2$— group, or a —(CH$_2$)$_{n-1}$—C(=O)— group, where n is an integer between 2 and 6 and Ar comprises an aromatic group.

18. An electrophotographic imaging apparatus according to claim 17 wherein the aryl group or the aromatic heterocyclic group is selected from the group consisting of the following formulae:

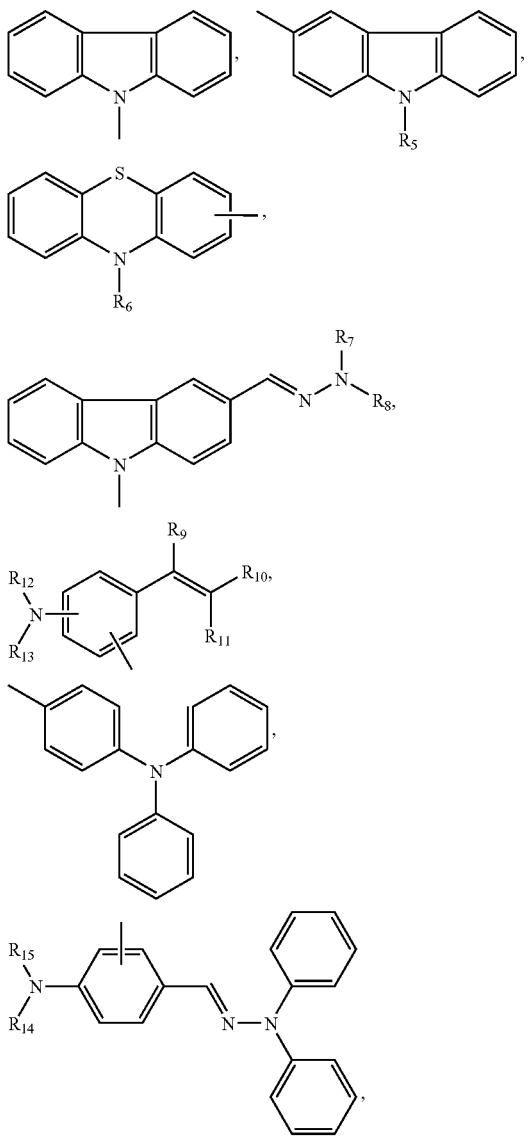

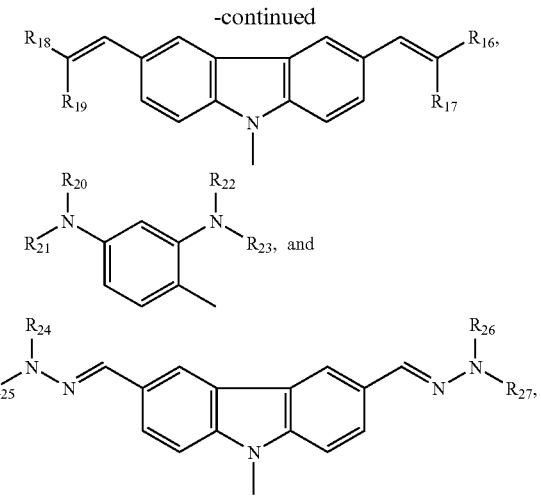

where R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, and R$_{27}$ comprise, each independently, H, an alkyl group, an alkenyl group, an alkynyl group, an acyl group, an aromatic group, or a heterocyclic group.

19. An electrophotographic imaging apparatus according to claim 18 wherein the aryl group or the aromatic heterocyclic group further comprises at least a substituent selected from the group consisting of an alkyl group, an alkenyl group, an alkynyl group, an acyl group, an aromatic group, a heterocyclic group, an (N,N-disubstituted)hydrazone group, an enamine group, and an azine group.

20. An electrophotographic imaging apparatus according to claim 12 wherein the photoconductive element further comprises a second charge transport material.

21. An electrophotographic imaging apparatus according to claim 20 wherein second charge transport material comprises an electron transport compound.

22. An electrophotographic imaging apparatus according to claim 12 further comprising a toner dispenser.

23. A charge transport material having the formula

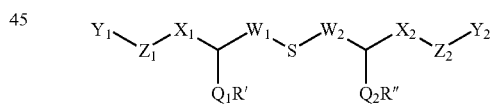

where Z$_1$ and Z$_2$ comprise, each independently, a vinyl group, or a —CR$_3$=N—N=CR$_4$— group;
Y$_1$ and Y$_2$ comprise, each independently, an aromatic group;
X$_1$ and X$_2$ are, each independently, a linking group;
W$_1$ and W$_2$ are, each independently, a —(CH$_2$)$_n$— group or a —(CH$_2$)$_{n-1}$—C(=O)— group, where n is an integer between 1 and 10, inclusive;
Q$_1$ and Q$_2$ are, each independently, O, S, or NR; and
R$_1$, R$_2$, R$_3$, R$_4$, R, R', and R" comprise, each independently, H, an alkyl group, an alkenyl group, an alkynyl group, an acyl group, a heterocyclic group, or an aromatic group.

24. A charge transport material according to claim 23 wherein Y$_1$ and Y$_2$ comprise, each independently, an aryl group selected from the group consisting of a phenyl group, a naphthyl group, a bis[(N,N-disubstituted)amino]aryl group, a julolidinyl group, an (N-substituted)arylamine group, and an (N,N-disubstituted)arylamine group.

25. A charge transport material according to claim 23 wherein $Y_1$ and $Y_2$ comprise, each independently, an aromatic heterocyclic group selected from the group consisting of a furanyl group, a thiophenyl group, a pyrrolyl group, an indolyl group, a carbazolyl group, a benzofuranyl group, a benzothiophenyl group, a dibenzofuranyl group, a dibenzothiophenyl group, a pyridinyl group, a pyridazinyl group, a pyrimidinyl group, a pyrazinyl group, a triazinyl group, a tetrazinyl group, a petazinyl group, a quinolinyl group, an isoquinolinyl group, a cinnolinyl group, a phthalazinyl group, a quinazolinyl group, a quinoxalinyl group, a naphthyridinyl group, an acridinyl group, a phenanthridinyl group, a phenanthrolinyl group, an anthyridinyl group, a purinyl group, a pteridinyl group, an alloxazinyl group, a phenazinyl group, a phenothiazinyl group, a phenoxazinyl group, a phenoxathiinyl group, a dibenzo(1,4)dioxinyl group, a thianthrenyl group, a bicarbazolyl group, and a 1,6-di(10H-10-phenothiazinyl)hexyl group.

26. A charge transport material according to claim 24 wherein the aryl group further comprises at least a substituent selected from the group consisting of an alkyl group, an alkenyl group, an alkynyl group, an acyl group, an aromatic group, a heterocyclic group, an amino group, an (N,N-disubstituted)hydrazone group, an enamine group, an azine group, an epoxy group, a thiiranyl group, and an aziridinyl group.

27. A charge transport material according to claim 23 wherein $X_1$ and $X_2$ are, each independently, a —$(CH_2)_m$— group, where m is an integer between 1 and 20, inclusive, and one or more of the methylene groups is optionally replaced by O, S, N, C, B, Si, P, C=O,O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkylsulfanyl group, an alkenyl group, an alkynyl group, an acyl group, a heterocyclic group, an aromatic group, or a part of a ring group.

28. A charge transport material according to claim 27 wherein $X_1$ and $X_2$ are, each independently, a —$CH_2$— group, a —$OCH_2$— group, or a —Ar—$OCH_2$— group; $Y_1$ and $Y_2$ comprise, each independently, an aryl group or an aromatic heterocyclic group; and $W_1$ and $W_2$ are, each independently, a bond, a —$CH_2$— group, a —$CH_2CH_2$— group, or a —$(CH_2)_{n-1}$—C(=O)— group, where n is an integer between 2 and 6 and Ar comprises an aromatic group.

29. A charge transport material according to claim 28 wherein the aryl group or the aromatic heterocyclic group is selected from the group consisting of the following formulae:

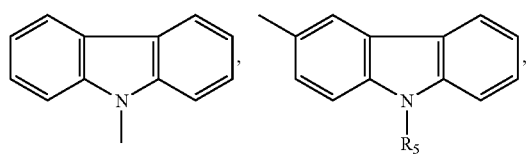

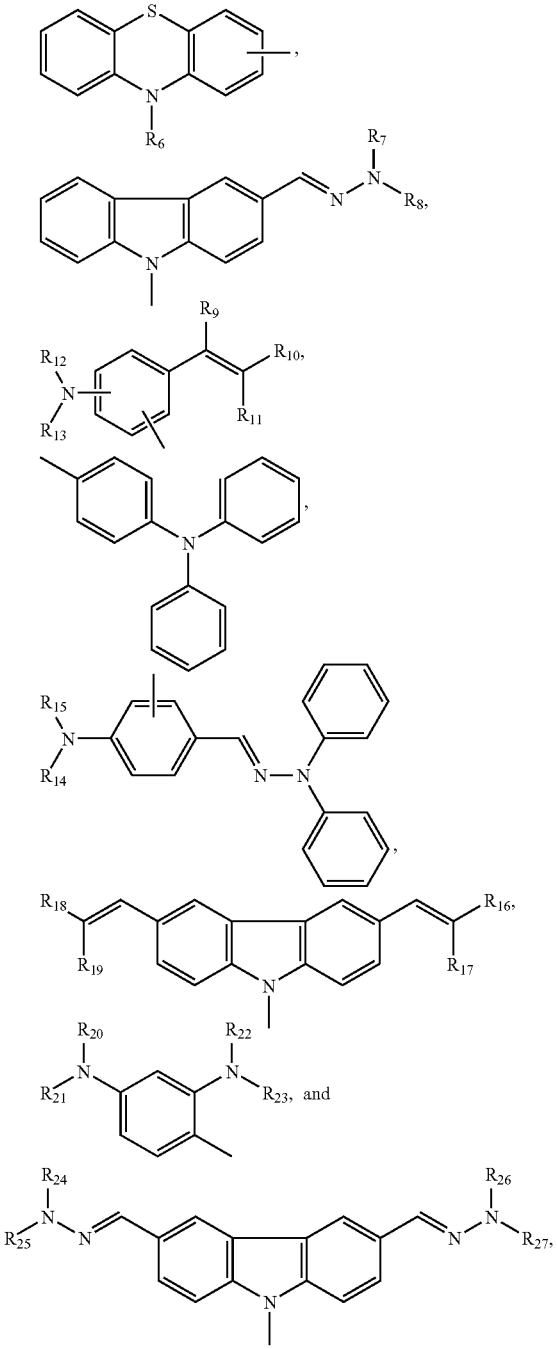

where $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$ comprise, each independently, H, an alkyl group, an alkenyl group, an alkynyl group, an acyl group, an aromatic group, or a heterocyclic group.

30. A charge transport material according to claim 19 wherein the aryl group or the aromatic heterocyclic group further comprises at least a substituent selected from the group consisting of an alkyl group, an alkenyl group, an alkynyl group, an acyl group, an aromatic group, a heterocyclic group, an (N,N-disubstituted)hydrazone group, an enamine group, and an azine group.

* * * * *